(12) United States Patent
Zhang et al.

(10) Patent No.: US 7,655,683 B2
(45) Date of Patent: Feb. 2, 2010

(54) IMIDAZOLOPYRAZOLE DERIVATIVES USEFUL AS SELECTIVE ANDROGEN RECEPTOR MODULATORS

(75) Inventors: Xuqing Zhang, Exton, PA (US); Zhihua Sui, Exton, PA (US)

(73) Assignee: Janssen Pharmaceutica NV, Beerse (BE)

( * ) Notice: Subject to any disclaimer, the term of this patent is extended or adjusted under 35 U.S.C. 154(b) by 358 days.

(21) Appl. No.: 11/670,046

(22) Filed: Feb. 1, 2007

(65) Prior Publication Data

US 2007/0197616 A1   Aug. 23, 2007

Related U.S. Application Data

(60) Provisional application No. 60/772,026, filed on Feb. 10, 2006.

(51) Int. Cl.
*A61K 31/4162* (2006.01)
*A61K 31/4188* (2006.01)
*C07D 235/00* (2006.01)
*C07D 231/00* (2006.01)

(52) U.S. Cl. .................. 514/393; 514/407; 548/303.1; 548/360.5

(58) Field of Classification Search ............... 548/303.1, 548/360.5; 514/393, 407
See application file for complete search history.

(56) References Cited

U.S. PATENT DOCUMENTS

2006/0211756 A1   9/2006   Zhang et al.

FOREIGN PATENT DOCUMENTS

| WO | WO 01/30781 A2 | 5/2001 |
| WO | WO 03/096980 A2 | 11/2003 |
| WO | WO 2005/087232 A1 | 9/2005 |
| WO | WO 2005/089118 A2 | 9/2005 |

OTHER PUBLICATIONS

International Search Report for PCT International Application No. PCT/US2007/061436 dated May 21, 2007.
Basaria, S. et al.: "Anabolic-Androgenic Steroid Therapy in the Treatment of Chronic Diseases"; The J. of Clin. Endocrin. & Metab. (2001) 86(11): 5108-5117.
Newling, D.W.W.: "Anti-androgens in the treatment of prostate cancer"; British J. of Urology (1996) 77: 776-784.
Shahidi, N.T., MD: "A Review of the Chemistry, Biological Action, and Clinical Applications of Anabolic-Androgenic Steroids"; Clinical Therapeutics (2001) 23(9): 1355-1390.
Zhang, X. et al.: "Synthesis and SAR of novel hydantoin derivatives as selective androgen receptor modulators"; Elsevier, Bioorganic & Med. Chem. Letters (2006) 16: 5763-5766.
Zhang, X. et al.: "Serendipitous discovery of novel imidazolopyrazole scaffold as selective androgen receptor modulators"; Elsevier, Bioorganic & Med. Chem. Letters (2007) 17: 439-443.

*Primary Examiner*—Rebecca L Anderson
*Assistant Examiner*—Jason Nolan

(57) ABSTRACT

The present invention is directed to novel imidazolopyrazole derivatives, pharmaceutical compositions containing them and their use in the treatment of disorders and conditions modulated by the androgen receptor.

9 Claims, No Drawings

IMIDAZOLOPYRAZOLE DERIVATIVES USEFUL AS SELECTIVE ANDROGEN RECEPTOR MODULATORS

CROSS REFERENCE TO RELATED APPLICATIONS

This application claims the benefit of U.S. Provisional Application 60/772,026, filed on Feb. 10, 2006, which is incorporated by reference herein in its entirety.

FIELD OF THE INVENTION

The present invention is directed to novel imidazolopyrazole derivatives, pharmaceutical compositions containing them and their use in the treatment of disorders mediated by one or more sex steroid hormone receptors and processes for their preparation. The compounds of the present invention are selective androgen receptor modulators.

BACKGROUND OF THE INVENTION

Androgens are the anabolic steroid hormones of animals that control muscle and skeletal mass, the maturation of the reproductive system, the development of secondary sexual characteristics and the maintenance of fertility in the male. In women, testosterone is converted to estrogen in most target tissues, but androgens themselves may play a role in normal female physiology, for example, in the brain. The chief androgen found in serum is testosterone, and this is the effective compound in tissues such as the testes and pituitary. In prostate and skin, testosterone is converted to dihydrotestosterone (DHT) by the action of 5α-reductase. DHT is a more potent androgen than testosterone because it binds more strongly to the androgen receptor.

Like all steroid hormones, androgens bind to a specific receptor inside the cells of target tissues, in this case the androgen receptor. This is a member of the nuclear receptor transcription factor family. Binding of androgen to the receptor activates it and causes it to bind to DNA binding sites adjacent to target genes. From there it interacts with co-activator proteins and basic transcription factors to regulate the expression of the gene. Thus, via its receptor, androgens cause changes in gene expression in cells. These changes ultimately have consequences on the metabolic output, differentiation or proliferation of the cell that are visible in the physiology of the target tissue.

Although modulators of androgen receptor function have been employed clinically for some time, both the steroidal (Basaria, S., Wahlstrom, J. T., Dobs, A. S., *J. Clin Endocrinol Metab* (2001), 86, pp 5108-5117; Shahidi, N. T., *Clin Therapeutics*, (2001), 23, pp 1355-1390), and non-steroidal (Newling, D. W., *Br. J. Urol.*, 1996, 77 (6), pp 776-784) compounds have significant liabilities related to their pharmacological parameters, including gynecomastia, breast tenderness and hepatoxicity. In addition, drug-drug interactions have been observed in patients receiving anticoagulation therapy using coumarins. Finally, patients with aniline sensitivities could be compromised by the metabolites of non-steroidal antiandrogens.

Non-steroidal agonists and antagonists of the androgen receptor are useful in the treatment of a variety of disorders and diseases. More particularly, antagonists of the androgen receptor can be employed in the treatment of prostate cancer, benign prostatic hyperplasia, hirsutism in women, alopecia, anorexia nervosa, breast cancer and acne. Agonists of the androgen receptor can be employed in male contraception, male performance enhancement, as well as in the treatment of cancer, AIDS, cachexia, and other disorders.

Nonetheless, there exists a need for small molecule, non-steroidal antagonists of the androgen receptor. We now describe a novel series of imidazolopyrazole derivatives as androgen receptor modulators.

SUMMARY OF THE INVENTION

The present invention is directed to a compound of formula (I)

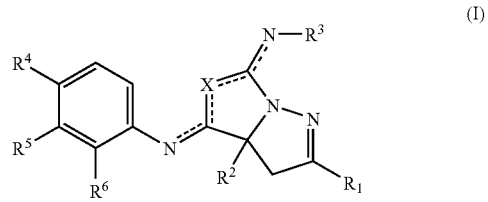

(I)

wherein:

$R^1$ is selected from the group consisting of hydrogen, carboxy, alkyl, halogenated $C_{1-4}$alkyl, hydroxy substituted $C_{1-4}$alkyl, cycloalkyl, aryl, aralkyl, heteroaryl, heteroarylalkyl-, heterocycloalkyl, heterocycloalkyl-alkyl-, —C(O)-alkyl, —C(O)-(halogenated $C_{1-4}$alkyl), —C(O)O—$C_{1-4}$alkyl, —C(O)O-aryl, —$C_{1-4}$alkyl-S(O)$_{0-2}$—$C_{1-4}$alkyl, t-butyl-dimethyl-silyl and trimethylsilyl;

wherein the aryl, cycloalkyl, heteroaryl or heterocycloalkyl, whether alone or as part of a substituent group is optionally substituted with one or more substituents independently selected from the group consisting of halogen, hydroxy, $C_{1-4}$alkyl, $C_{1-4}$alkoxy, halogenated $C_{1-4}$alkyl, halogenated $C_{1-4}$alkoxy, cyano, nitro, amino, $C_{1-4}$alkylamino, di($C_{1-4}$alkyl)amino, —$NR^C$—C(O)—$C_{1-4}$alkyl, $NR^C$—C(O)-(halogenated $C_{1-4}$alkyl), —C(O)O—$C_{1-4}$alkyl, —S(O)$_{0-2}$—$C_{1-4}$alkyl, —SO$_2$—$NR^CR^D$, trimethyl-silyl and t-butyl-dimethyl-silyloxy; wherein each $R^C$ and $R^D$ are each independently selected from hydrogen or $C_{1-4}$alkyl;

$R^2$ is selected from the group consisting of $C_{1-4}$alkyl, halogenated $C_{1-4}$alkyl;

X is O or NH;

$R^3$ is selected from the group consisting of $C_{1-4}$alkyl, halogenated $C_{1-4}$alkyl, —C(O)—$C_{1-4}$alkyl, —S(O)$_{0-2}$—$C_{1-4}$alkyl, —C(O)—$NR^A$—$C_{1-4}$alkyl, benzyl, —C(O)-phenyl and —S(O)$_{0-2}$-phenyl and —C(O)—$NR^A$-phenyl; wherein $R^A$ is hydrogen or $C_{1-4}$alkyl;

$R^4$ is absent or is selected from the group consisting of hydrogen, halogen, $C_{1-4}$alkyl, halogenated $C_{1-4}$alkyl, cyano, nitro, amino, $C_{1-4}$alkylamino, di($C_{1-4}$alkyl)amino, —O—$C_{1-4}$alkyl, —S(O)$_{0-2}$—$C_{1-4}$alkyl, —$NR^B$—C(O)—$C_{1-4}$alkyl, benzyl, —O-phenyl, —C(O)-phenyl and —S(O)$_{0-2}$-phenyl; wherein $R^B$ is hydrogen or $C_{1-4}$alkyl;

$R^5$ is absent or is selected from the group consisting of hydrogen, halogen, $C_{1-4}$alkyl, halogenated $C_{1-4}$alkyl, cyano, nitro, amino, $C_{1-4}$alkylamino, di($C_{1-4}$alkyl)amino, —O—$C_{1-4}$alkyl, —S(O)$_{0-2}$—$C_{1-4}$alkyl, —$NR^B$—C(O)—$C_{1-4}$alkyl, benzyl, —O-phenyl, —C(O)-phenyl and —S(O)$_{0-2}$-phenyl; wherein $R^B$ is hydrogen or $C_{1-4}$alkyl;

$R_6$ is absent or selected from the group consisting of hydrogen, halogen, $C_{1-4}$alkyl, halogenated $C_{1-4}$alkyl, cyano, nitro, amino, —O—$C_{1-4}$alkyl and —S(O)$_{0-2}$—$C_{1-4}$alkyl;

or pharmaceutically acceptable salts and hydrates thereof.

Illustrative of the invention is a pharmaceutical composition comprising a pharmaceutically acceptable carrier and any of the compounds described herein. An illustration of the invention is a pharmaceutical composition made by mixing any of the compounds described herein and a pharmaceutically acceptable carrier. Illustrating the invention is a process for making a pharmaceutical composition comprising mixing any of the compounds described herein and a pharmaceutically acceptable carrier.

Exemplifying the invention are methods of treating disorders and conditions modulated by the androgen receptor in a subject in need thereof comprising administering to the subject a therapeutically effective amount of any of the compounds or pharmaceutical compositions described herein.

An example of the invention is a method for treating an androgen receptor modulated disorder selected from the group consisting of prostate carcinoma, benign prostatic hyperplasia, hirsutism, or for male contraception, in a subject in need thereof comprising administering to the subject an effective amount of any of the compounds or pharmaceutical compositions described herein.

Another example of the invention is the use of any of the compounds described herein in the preparation of a medicament for treating: (a) prostate carcinoma, (b) benign prostatic hyperplasia, (c) hirsutism, (d) alopecia, (e) anorexia nervosa, (f) breast cancer, (g) acne, (h) AIDS, (i) cachexia, for (j) male contraception, or for (k) male performance enhancement, in a subject in need thereof.

DETAILED DESCRIPTION OF THE INVENTION

The present invention is directed to compounds of formula (I)

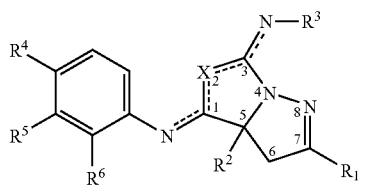

wherein $R^1$, $R^2$, $R^3$, $R^4$, $R^5$, $R^6$ and X are as herein defined, useful as selective androgen receptor modulators for the treatment of prostate carcinoma, benign prostatic hyperplasia (BPH), hirsutism, alopecia, anorexia nervosa, breast cancer, acne, AIDS, cachexia, as a male contraceptive, and/or as a male performance enhancer.

In an embodiment of the present invention, $R^1$ is selected from the group consisting of hydrogen, carboxy, alkyl, halogenated $C_{1-4}$alkyl, aryl, aralkyl, heteroaryl, —C(O)—$C_{1-4}$alkyl, —C(O)-(halogenated $C_{1-4}$alkyl), —C(O)O—$C_{1-4}$alkyl and —C(O)O-aryl;

wherein the aryl or heteroaryl, whether alone or as part of a substituent group is optionally substituted with one or more substituents independently selected from the group consisting of halogen, hydroxy, $C_{1-4}$alkyl, $C_{1-4}$alkoxy, halogenated $C_{1-4}$alkyl, cyano, nitro and —C(O)O—$C_{1-4}$alkyl;

Preferably, $R^1$ is selected from the group consisting of hydrogen, methyl, trifluoromethyl, 2,3,4,5,6-pentafluorophenyl, 4-methyl-carbonyl-amino-phenyl, 4-(trifluoromethyl-carbonyl-amino)-phenyl and ethoxy-carbonyl. Preferably, $R^1$ is selected from the group consisting of trifluoromethyl and 4-methyl-carbonyl-aminophenyl; more preferably, $R^1$ is trifluoromethyl.

In an embodiment of the present invention, $R^2$ is selected from the group consisting of $C_{1-2}$alkyl and halogenated $C_{1-2}$alkyl. Preferably, $R^2$ is selected from the group consisting of methyl and ethyl. More preferably still, $R^2$ is methyl.

In an embodiment of the present invention, $R^3$ is absent or selected from the group consisting of $C_{1-4}$alkyl, halogenated $C_{1-4}$alkyl, —C(O)—$C_{1-4}$alkyl, —C(O)—NH—$C_{1-4}$alkyl, —C(O)—NH-phenyl and —C(O)-phenyl. Preferably, $R^3$ is absent or selected from the group consisting of —C(O)—$C_{1-4}$ alkyl and —C(O)—NH-phenyl. More preferably, $R^3$ is absent or selected from the group consisting of —C(O)-trifluoromethyl and —C(O)—NH-phenyl. More preferably, $R^3$ is H.

In an embodiment of the present invention, $R^4$ is selected from the group consisting of hydrogen, halogen, halogenated $C_{1-4}$alkyl, cyano, nitro, benzyl, —O—$C_{1-4}$alkyl-, —O-phenyl, —C(O)-phenyl, —S(O)$_{0-2}$—$C_{1-4}$alkyl and —S(O)$_{0-2}$-phenyl. In another embodiment of the present invention, $R^4$ is absent or selected from the group consisting of halogen, cyano, nitro and —S(O)$_{0-2}$—$C_{1-4}$alkyl. Preferably, $R^4$ is absent or selected from the group consisting of chloro, bromo, cyano, nitro and —SO$_2$-methyl . More preferably, $R^4$ is selected from the group consisting of chloro, bromo, cyano and nitro. More preferably, $R^4$ is cyano.

In an embodiment of the present invention, $R^5$ is absent or selected from the group consisting of hydrogen, halogen, halogenated $C_{1-4}$alkyl, cyano, nitro, benzyl, —O-phenyl, —C(O)-phenyl, —S(O)$_{0-2}$—$C_{1-4}$alkyl and —S(O)$_{0-2}$-phenyl. In another embodiment of the present invention, $R^5$ is absent or selected from the group consisting of hydrogen, halogen, halogenated $C_{1-4}$alkyl and cyano. Preferably, $R^5$ is absent or selected from the group consisting of hydrogen, chloro, trifluoromethyl and cyano. More preferably, $R^5$ is trifluoromethyl.

In an embodiment of the present invention, $R^5$ is absent or selected from the group consisting of halogen, $C_{1-4}$alkyl, halogenated $C_{1-4}$alkyl, —O—$C_{1-4}$alkyl- and —S(O)$_{0-2}$—$C_{1-4}$alkyl; Preferably, $R^6$ is absent or selected from the group consisting of $C_{1-4}$alkyl and halogenated $C_{1-4}$alkyl. More preferably, $R^6$ is absent or selected from the group consisting of methyl and ethyl. More preferably, $R^6$ is H.

In yet another embodiment of the present invention are hydrates of formula (I). The hydrate structure of formula (1) is presented below, wherein a covalent bond is formed between C1, C3 or C7 and $H_2O$.

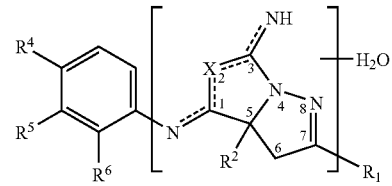

Hydrates of Formula (I)

In an embodiment of the present invention are compounds of formula (I) selected from the group consisting of 4-(6-amino-3a-methyl-2-trifluoromethyl-3,3a-dihydro-imidazo [1,5-b]pyrazol-4-ylideneamino)-2-trifluoromethyl-benzonitrile, 4-(6-amino-3aR-methyl-2-trifluoromethyl-3,3a-dihydro-imidazo[1,5-b]pyrazol-4-ylideneamino)-2-trifluoromethyl-benzonitrile, 3a-methyl-4-(4-nitro-3-trifluoromethyl-phenylimino)-2-trifluoromethyl-3a,4-dihydro-3H-imidazo[1,5-b]pyrazol-6-ylamine, hydrates of 4-(6-amino-3aR-methyl-2-trifluoromethyl-3,3a-dihydro-imidazo[1,5-b]pyrazol-4-ylideneamino)-2-trifluoromethylbenzonitrile, hydrates of 4-(6-amino-3aS-methyl-2-trifluoromethyl-3,3a-dihydro-imidazo[1,5-b]pyrazol-4-ylideneamino)-2-trifluoromethyl-benzonitrile and pharmaceutically acceptable salts thereof.

In another embodiment of the present invention is any single compound or subset of compounds selected from the representative compounds listed in Tables 1-2 below.

Additional embodiments of the present invention, include those wherein the substituents selected for one or more of the variables defined herein (i.e. $R^1$, $R^2$, $R^3$, $R^4$, $R^5$, $R^6$, and X) are independently selected to be any individual substituent or any subset of substituents selected from the complete list as defined herein.

Representative compounds of the present invention are as listed in Table 1-2 below. Unless otherwise noted, wherein a stereogenic center is present in the listed compound, the compound was prepared as a mixture of stereo-configurations. Where a stereogenic center is present, the S and R designations are intended to indicate that the exact stereo-configuration of the center has been determined. The S* and R* designations are intended to indicate that the exact stereo-configuration of the center has not been determined. The rac designation is intended to indicate that the stereo-configuration of the center is a racemic mixture.

TABLE 1

Representative Compounds of Formula (I)

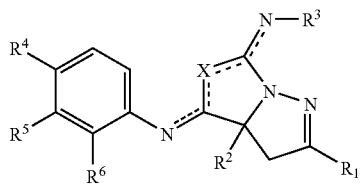

| X | ID | $R^1$ | $R^2$ | $R^3$ | $R^4$ | $R^5$ | $R^6$ |
|---|---|---|---|---|---|---|---|
| X = N | 1 | trifluoromethyl | methyl | H | cyano | trifluoromethyl | H |
| X = N | 2 | trifluoromethyl | R-methyl | H | cyano | trifluoromethyl | H |
| X = N | 3 | trifluoromethyl | S-methyl | H | cyano | trifluoromethyl | H |
| X = N | 4 | trifluoromethyl | methyl | H | chloro | chloro | H |
| X = N | 5 | trifluoromeethyl | methyl | H | nitro | trifluoromethyl | H |
| X = N | 6 | H | methyl | H | cyano | trifluoromethyl | H |
| X = N | 7 | ethoxycarbonyl | methyl | H | cyano | trifluoromethyl | H |
| X = N | 8 | trifluoromethyl | ethyl | H | cyano | trifluoromethyl | H |
| X = N | 9 | trifluoromethyl | methyl | H | cyano | trifluoromethyl | ethyl |
| X = N | 10 | trifluoromethyl | methyl | H | bromo | trifluoromethyl | H |
| X = N | 11 | 2,3,4,5,6-pentafluoropheny | methyl | H | cyano | trifluoromethyl | H |
| X = N | 12 | trifluoromethyl | methyl | (R)-4-(2,2,2-trifluoro-1-methoxy-1-phenyl-ethyl)-benzoyl | cyano | trifluoromethyl | H |
| X = N | 13 | trifluoromethyl | methyl | trifluoromethyl-canbonyl | cyano | trifluoro methyl | H |
| X = N | 14 | trifluoromethyl | methyl | (4-iodo-phenyl)-carbamic | cyano | trifluoromethyl | H |
| X = O | 15 | trifluoromethyl | methyl | H | cyano | trifluoromethyl | H |

TABLE 2

Representative Compounds of Hydrates of Formula (I)

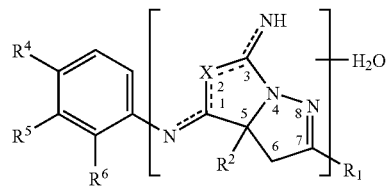

| JNJ No | ID | $R^1$ | $R^2$ | OH | $R^4$ | $R^5$ | $R^6$ |
|---|---|---|---|---|---|---|---|
| X = N | 16 | trifluoromethyl | R-methyl | C1 (R*) | cyano | trifluoromethyl | H |
| X = N | 17 | trifluoromethyl | R-methyl | C1 (S*) | cyano | trifluoromethyl | H |
| X = N | 18 | trifluoromethyl | S-methyl | C1 (S*) | cyano | trifluoromethyl | H |
| X = N | 19 | trifluoromethyl | S-methyl | C1 (R*) | cyano | trifluoromethyl | H |
| X = N | 20 | trifluoromethyl | R-methyl | C3 (rac) | cyano | trifluoromethyl | H |
| X = N | 21 | trifluoromethyl | S-methyl | C3 (rac) | cyano | trifluoromethyl | H |

As used herein, "halogen" shall mean chlorine, bromine, fluorine and iodine.

As used herein, the term "alkyl" whether used alone or as part of a substituent group, include straight and branched chains. For example, alkyl radicals include methyl, ethyl, propyl, isopropyl, butyl, isobutyl, sec-butyl, t-butyl, pentyl and the like. Unless otherwise noted, "lower" when used with alkyl means a carbon chain composition of 1-4 carbon atoms.

As used herein, unless otherwise noted, the term "halogenated $C_{1-4}$alkyl" shall mean any straight or branched alkyl chain comprising one to four carbon atoms wherein the alkyl chain is substituted with one or more, preferably one to five, more preferably one to three halogen atoms, and wherein the halogen atoms are independently selected from chloro, bromo, fluoro or iodo, preferably chloro or fluoro, more preferably fluoro. Suitable examples include, but are not limited to trifluoromethyl, 2,2,2-trilfuoroethyl, 1,1,2,2,2-pentafluoroethyl, and the like.

As used herein, unless otherwise noted, "alkoxy" shall denote an oxygen ether radical of the above described straight or branched chain alkyl groups. For example, methoxy, ethoxy, n-propoxy, sec-butoxy, t-butoxy, n-hexyloxy and the like.

As used herein, unless otherwise noted, "aryl" shall refer to unsubstituted carbocylic aromatic groups such as phenyl, naphthyl, and the like.

As used herein, unless otherwise noted, the term "cycloalkyl" shall mean any stable 3-8 membered monocyclic, saturated ring system, for example cyclopropyl, cyclobutyl, cyclopentyl, cyclohexyl, cycloheptyl and cyclooctyl.

As used herein, unless otherwise noted, "heteroaryl" shall denote any five or six membered monocyclic aromatic ring structure containing at least one heteroatom selected from the group consisting of O, N and S, optionally containing one to three additional heteroatoms independently selected from the group consisting of O, N and S; or a nine or ten membered bicyclic aromatic ring structure containing at least one heteroatom selected from the group consisting of O, N and S, optionally containing one to four additional heteroatoms independently selected from the group consisting of O, N and S. The heteroaryl group may be attached at any heteroatom or carbon atom of the ring such that the result is a stable structure.

Examples of suitable heteroaryl groups include, but are not limited to, pyrrolyl, furyl, thienyl, oxazolyl, imidazolyl, purazolyl, isoxazolyl, isothiazolyl, triazolyl, thiadiazolyl, pyridyl, pyridazinyl, pyrimidinyl, pyrazinyl, pyranyl, furazanyl, indolizinyl, indolyl, isoindolinyl, indazolyl, benzofuryl, benzothienyl, benzimidazolyl, benzthiazolyl, purinyl, quinolizinyl, quinolinyl, isoquinolinyl, isothiazolyl, cinnolinyl, phthalazinyl, quinazolinyl, quinoxalinyl, naphthyridinyl, pteridinyl, and the like.

As used herein, the term "heterocycloalkyl" shall denote any five to seven membered monocyclic, saturated or partially unsaturated ring structure containing at least one heteroatom selected from the group consisting of O, N and S, optionally containing one to three additional heteroatoms independently selected from the group consisting of O, N and S; or a nine to ten membered saturated, partially unsaturated or partially aromatic bicyclic ring system containing at least one heteroatom selected from the group consisting of O, N and S, optionally containing one to four additional heteroatoms independently selected from the group consisting of O, N and S. The heterocycloalkyl group may be attached at any heteroatom or carbon atom of the ring such that the result is a stable structure.

Examples of suitable heterocycloalkyl groups include, but are not limited to, pyrrolinyl, pyrrolidinyl, dioxalanyl, imidazolinyl, imidazolidinyl, pyrazolinyl, pyrazolidinyl, piperidinyl, dioxanyl, morpholinyl, dithianyl, thiomorpholinyl, piperazinyl, trithianyl, indolinyl, chromenyl, 3,4-methylenedioxyphenyl, 2,3-dihydrobenzofuryl, and the like.

As used herein, the notation "*" shall denote the presence of a stereogenic center.

When a particular group is "substituted" (e.g., alkyl, aryl, cycloalkyl, heterocycloalkyl, heteroaryl), that group may have one or more substituents, preferably from one to five substituents, more preferably from one to three substituents, most preferably from one to two substituents, independently selected from the list of substituents.

With reference to substituents, the term "independently" means that when more than one of such substituents is possible, such substituents may be the same or different from each other.

To provide a more concise description, some of the quantitative expressions given herein are not qualified with the term "about". It is understood that whether the term "about" is used explicitly or not, every quantity given herein is meant to refer to the actual given value, and it is also meant to refer to the approximation to such given value that would reasonably be inferred based on the ordinary skill in the art, including approximations due to the experimental and/or measurement conditions for such given value.

As used herein, unless otherwise noted, the term "aprotic solvent" shall mean any solvent that does not yield a proton. Suitable examples include, but are not limited to DMF, dioxane, THF, acetonitrile, pyridine, dichloroethane, dichloromethane, MTBE, toluene, and the like.

As used herein, unless otherwise noted, the term "leaving group" shall mean a charged or uncharged atom or group which departs during a substitution or displacement reaction. Suitable examples include, but are not limited to, Br, Cl, I, mesylate, tosylate, and the like.

As used herein, unless otherwise noted, the term "nitrogen protecting group" shall mean a group which may be attached to a nitrogen atom to protect said nitrogen atom from participating in a reaction and which may be readily removed following the reaction. Suitable nitrogen protecting groups include, but are not limited to carbamates—groups of the formula —C(O)O—R wherein R is for example methyl, ethyl, t-butyl, benzyl, phenylethyl, $CH_2$=CH—$CH_2$—, and the like; amides—groups of the formula —C(O)—R' wherein R' is for example methyl, phenyl, trifluoromethyl, and the like; N-sulfonyl derivatives—groups of the formula —$SO_2$—R" wherein R" is for example tolyl, phenyl, trifluoromethyl, 2,2,5,7,8-pentamethylchroman-6-yl-, 2,3,6-trimethyl-4-methoxybenzene, and the like. Other suitable nitrogen protecting groups may be found in texts such as T. W. Greene & P. G. M. Wuts, *Protective Groups in Organic Synthesis*, John Wiley & Sons, 1991.

Under standard nomenclature used throughout this disclosure, the terminal portion of the designated side chain is described first, followed by the adjacent functionality toward the point of attachment. Thus, for example, a "phenyl$C_1$-

$C_6$alkylaminocarbonyl$C_1$-$C_6$alkyl" substituent refers to a group of the formula

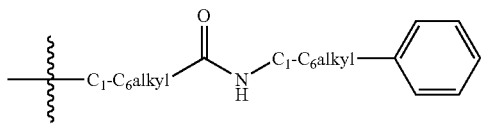

Abbreviations used in the specification, particularly the Schemes and Examples, are as follows:
Ac=Acetyl (i.e. —C(O)CH$_3$)
AcOH=Acetic acid
CSA=Camphor sulfonic acid
DCM=Dichloromethane
DIPEA or DIEA=Diisopropylethylamine
DMA N,N-Dimethylacetamide
DMF=N,N-Dimethylformamide
DMSO=Dimethylsulfoxide
Et$_3$N=Triethylamine
Et$_2$O=Diethyl ether
EtOAc=Ethyl acetate
MeOH=Methanol
Ms=Methylsulfonic
PTSA or pTSA=p-Toluene sulfonic acid
TEA=Triethylamine
TFA=Trifluoroacetic Acid
TFAA=Trifluoroacetic acid anhydride
THF=Tetrahydrofuran
Ts=tosyl (—SO$_2$-(p-toluene))

The term "subject" as used herein, refers to an animal, preferably a mammal, most preferably a human, who has been the object of treatment, observation or experiment.

The term "therapeutically effective amount" as used herein, means that amount of active compound or pharmaceutical agent that elicits the biological or medicinal response in a tissue system, animal or human that is being sought by a researcher, veterinarian, medical doctor or other clinician, which includes alleviation of the symptoms of the disease or disorder being treated.

As used herein, the term "composition" is intended to encompass a product comprising the specified ingredients in the specified amounts, as well as any product which results, directly or indirectly, from combinations of the specified ingredients in the specified amounts.

Where the compounds according to this invention have at least one chiral center, they may accordingly exist as enantiomers. Where the compounds possess two or more chiral centers, they may additionally exist as diastereomers. It is to be understood that all such isomers and mixtures thereof are encompassed within the scope of the present invention. Furthermore, some of the crystalline forms for the compounds may exist as polymorphs and as such are intended to be included in the present invention. In addition, some of the compounds may form solvates with water (i.e., hydrates) or common organic solvents, and such solvates are also intended to be encompassed within the scope of this invention.

The present invention includes within its scope prodrugs of the compounds of this invention. In general, such prodrugs will be functional derivatives of the compounds which are readily convertible in vivo into the required compound. Thus, in the methods of treatment of the present invention, the term "administering" shall encompass the treatment of the various disorders described with the compound specifically disclosed or with a compound which may not be specifically disclosed, but which converts to the specified compound in vivo after administration to the patient. Conventional procedures for the selection and preparation of suitable prodrug derivatives are described, for example, in "Design of Prodrugs", ed. H. Bundgaard, Elsevier, 1985.

For use in medicine, the salts of the compounds of this invention refer to non-toxic "pharmaceutically acceptable salts." Other salts may, however, be useful in the preparation of compounds according to this invention or of their pharmaceutically acceptable salts. Suitable pharmaceutically acceptable salts of the compounds include acid addition salts which may, for example, be formed by mixing a solution of the compound with a solution of a pharmaceutically acceptable acid such as hydrochloric acid, sulfuric acid, fumaric acid, maleic acid, succinic acid, acetic acid, benzoic acid, citric acid, tartaric acid, carbonic acid or phosphoric acid. Furthermore, where the compounds of the invention carry an acidic moiety, suitable pharmaceutically acceptable salts thereof may include alkali metal salts, e.g., sodium or potassium salts; alkaline earth metal salts, e.g., calcium or magnesium salts; and salts formed with suitable organic ligands, e.g., quaternary ammonium salts. Thus, representative pharmaceutically acceptable salts include the following:
acetate, benzenesulfonate, benzoate, bicarbonate, bisulfate, bitartrate, borate, bromide, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, oleate, pamoate (embonate), palmitate, pantothenate, phosphate/diphosphate, polygalacturonate, salicylate, stearate, sulfate, subacetate, succinate, tannate, tartrate, teoclate, tosylate, triethiodide and valerate.

Representative acids and bases which may be used in the preparation of pharmaceutically acceptable salts include the following:
acids including acetic acid, 2,2-dichloroactic acid, acylated amino acids, adipic acid, alginic acid, ascorbic acid, L-aspartic acid, benzenesulfonic acid, benzoic acid, 4-acetamidobenzoic acid, (+)-camphoric acid, camphorsulfonic acid, (+)-(1S)-camphor-10-sulfonic acid, capric acid, caproic acid, caprylic acid, cinnamic acid, citric acid, cyclamic acid, dodecylsulfuric acid, ethane-1,2-disulfonic acid, ethanesulfonic acid, 2-hydrocy-ethanesulfonic acid, formic acid, fumaric acid, galactaric acid, gentisic acid, glucoheptonic acid, D-gluconic acid, D-glucoronic acid, L-glutamic acid, α-oxo-glutaric acid, glycolic acid, hipuric acid, hydrobromic acid, hydrochloric acid, (+)-L-lactic acid, (±)-DL-lactic acid, lactobionic acid, maleic acid, (−)-L-malic acid, malonic acid, (±)-DL-mandelic acid, methanesulfonic acid, naphthalene-2-sulfonic acid, naphthalene-1,5-disulfonic acid, 1-hydroxy-2-naphthoic acid, nicotinc acid, nitric acid, oleic acid, orotic acid, oxalic acid, palmitric acid, pamoic acid, phosphoric acid, L-pyroglutamic acid, salicylic acid, 4-amino-salicylic acid, sebaic acid, stearic acid, succinic acid, sulfuric acid, tannic acid, (+)-L-tartaric acid, thiocyanic acid, p-toluenesulfonic acid and undecylenic acid; and bases including ammonia, L-arginine, benethamine, benzathine, calcium hydroxide, choline, deanol, diethanolamine, diethylamine, 2-(diethylamino)-ethanol, ethanolamine, ethylenediamine, N-methyl-glucamine, hydrabamine, 1H-imidazole, L-lysine, magnesium hydroxide, 4-(2-hydroxyethyl)-morpholine, piperazine, potassium hydroxide, 1-(2-hydroxyethyl)-pyrrolidine, secondary amine, sodium hydroxide, triethanolamine, tromethamine and zinc hydroxide.

Compounds of formula (I) may be prepared according to the process outlined in Scheme 1.

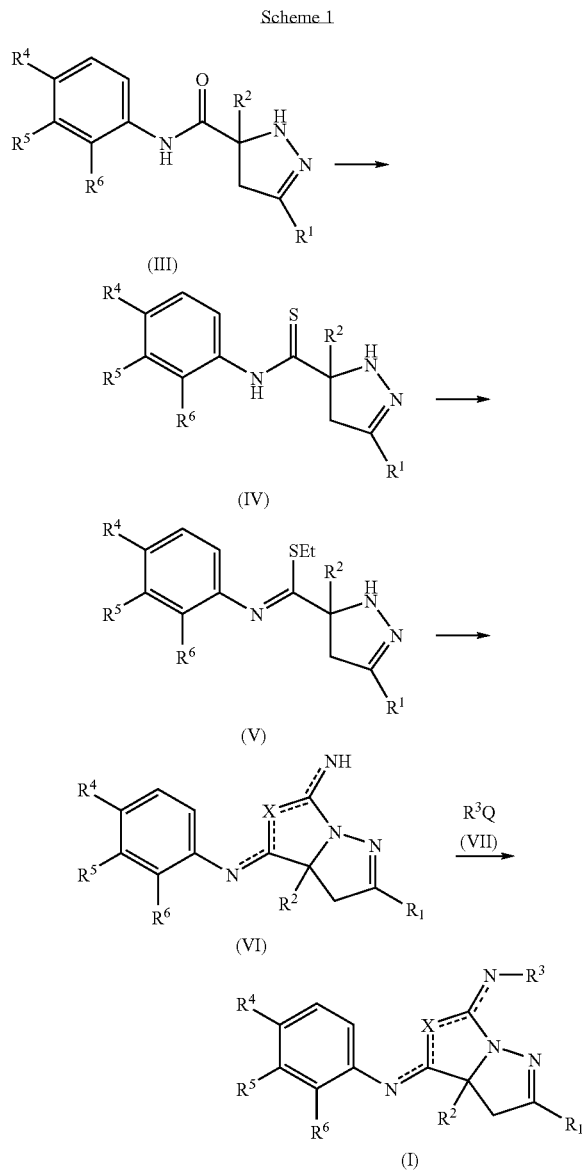

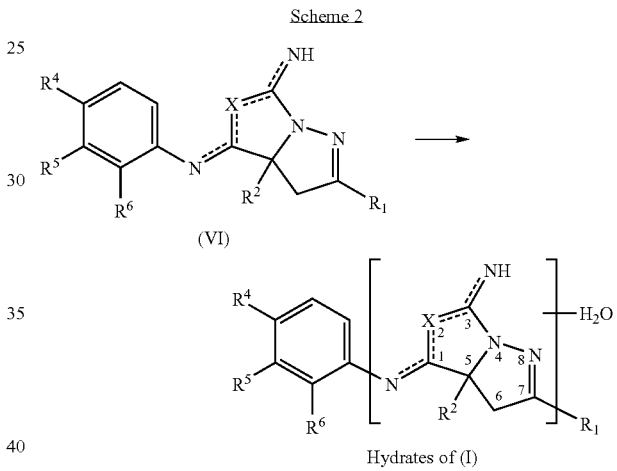

Accordingly, a suitably substituted compound of formula (III), a compound prepared according to co-pending U.S. application Ser. No. 11/258,448, filed Oct. 25, 2005, incorporated by reference herein in its entirety, is reacted with sulfur containing agent such as $S_8$, Lawsseson's agent, and the like, in an organic solvent such as toluene, xylene, dioxane, and the like, at a temperature in the range of from about 100° C. temperature to 150° C., preferably at a temperature in the range of from about 120 to about 140° C. to yield the corresponding compound of formula (IV).

The compound of formula (IV) is reacted with a alkylating agent such as EtI, $(EtO)_3{}^+BF_4{}^-$, EtOTf and the like, in the presence of a base such as $K_2CO_3$, NaH, potassium t-butoxide, and the like, in an organic solvent such as acetone, THF, dioxane, and the like, at a temperature in the range of from about room temperature to about reflux temperature, preferably at a temperature in the range of from about 50 to about 60° C., to yield the corresponding compound of formula (V).

The compound of formula (V) is further converted to the corresponding compound of formula (VI) by treating the compound of formula (V) with $NH_2CN$, in the presence of a base such as $K_2CO_3$, NaH, potassium t-butoxide, and the like, in an organic solvent such as dioxane, toluene, xylene and the like, at a temperature in the range of from about room temperature to about reflux temperature, preferably at a temperature in the range of from about 80 to about 100° C., to yield the corresponding compound of formula (VI).

The compound of formula (VI) is further, optionally reacted with a suitably substituted compound of formula $R^3Q$ (XI), wherein Q is a suitable leaving group such as halogen, OTs, OMs, and the like, a known compound or compound prepared by known methods, in an organic solvent such as THF, methylene chloride, dioxane, and the like, to yield the corresponding compound of formula (I).

Compounds of hydrates of formula (I) may be prepared according to the process outline in Scheme 2.

Accordingly, a suitably substituted compound of formula (VI) is treated with an acid such as HCl, pTSA, MsOH, and the like, in the presence of a mixed solvent containing 1:1 of THF, dioxane, and the like with water at a temperature in the range of about 0 to about 50° C., preferably at about room temperature, to yield the corresponding compound of hydrates of formula (I).

Where the processes for the preparation of the compounds according to the invention give rise to mixture of stereoisomers, these isomers may be separated by conventional techniques such as preparative chromatography. The compounds may be prepared in racemic form, or individual enantiomers may be prepared either by enantiospecific synthesis or by resolution. The compounds may, for example, be resolved into their component enantiomers by standard techniques, such as the formation of diastereomeric pairs by salt formation with an optically active acid, such as (−)-di-p-toluoyl-D-tartaric acid and/or (+)-di-p-toluoyl-L-tartaric acid followed by fractional crystallization and regeneration of the free base. The compounds may also be resolved by formation of diastereomeric esters or amides, followed by chromatographic separation and removal of the chiral auxiliary. Alternatively, the compounds may be resolved using a chiral HPLC column.

During any of the processes for preparation of the compounds of the present invention, it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 1991. The protecting groups may be removed at a convenient subsequent stage using methods known from the art.

The present invention further comprises pharmaceutical compositions containing one or more compounds of formula (I) and/or (II) with a pharmaceutically acceptable carrier. Pharmaceutical compositions containing one or more of the compounds of the invention described herein as the active ingredient can be prepared by intimately mixing the compound or compounds with a pharmaceutical carrier according to conventional pharmaceutical compounding techniques. The carrier may take a wide variety of forms depending upon the desired route of administration (e.g., oral, parenteral). Thus for liquid oral preparations such as suspensions, elixirs and solutions, suitable carriers and additives include water, glycols, oils, alcohols, flavoring agents, preservatives, stabilizers, coloring agents and the like; for solid oral preparations, such as powders, capsules and tablets, suitable carriers and additives include starches, sugars, diluents, granulating agents, lubricants, binders, disintegrating agents and the like. Solid oral preparations may also be coated with substances such as sugars or be enteric-coated so as to modulate major site of absorption. For parenteral administration, the carrier will usually consist of sterile water and other ingredients may be added to increase solubility or preservation. Injectable suspensions or solutions may also be prepared utilizing aqueous carriers along with appropriate additives.

To prepare the pharmaceutical compositions of this invention, one or more compounds of the present invention as the active ingredient is intimately admixed with a pharmaceutical carrier according to conventional pharmaceutical compounding techniques, which carrier may take a wide variety of forms depending of the form of preparation desired for administration, e.g., oral or parenteral such as intramuscular. In preparing the compositions in oral dosage form, any of the usual pharmaceutical media may be employed. Thus, for liquid oral preparations, such as for example, suspensions, elixirs and solutions, suitable carriers and additives include water, glycols, oils, alcohols, flavoring agents, preservatives, coloring agents and the like; for solid oral preparations such as, for example, powders, capsules, caplets, gelcaps and tablets, suitable carriers and additives include starches, sugars, diluents, granulating agents, lubricants, binders, disintegrating agents and the like. Because of their ease in administration, tablets and capsules represent the most advantageous oral dosage unit form, in which case solid pharmaceutical carriers are obviously employed. If desired, tablets may be sugar coated or enteric coated by standard techniques. For parenterals, the carrier will usually comprise sterile water, through other ingredients, for example, for purposes such as aiding solubility or for preservation, may be included. Injectable suspensions may also be prepared, in which case appropriate liquid carriers, suspending agents and the like may be employed. The pharmaceutical compositions herein will contain, per dosage unit, e.g., tablet, capsule, powder, injection, teaspoonful and the like, an amount of the active ingredient necessary to deliver an effective dose as described above. The pharmaceutical compositions herein will contain, per unit dosage unit, e.g., tablet, capsule, powder, injection, suppository, teaspoonful and the like, of from about 50-100 mg and may be given at a dosage of from about 0.5-5.0 mg/kg/day, preferably from about 1.0-3.0 mg/kg/day. The dosages, however, may be varied depending upon the requirement of the patients, the severity of the condition being treated and the compound being employed. The use of either daily administration or post-periodic dosing may be employed.

Preferably these compositions are in unit dosage forms from such as tablets, pills, capsules, powders, granules, sterile parenteral solutions or suspensions, metered aerosol or liquid sprays, drops, ampoules, autoinjector devices or suppositories; for oral parenteral, intranasal, sublingual or rectal administration, or for administration by inhalation or insufflation. Alternatively, the composition may be presented in a form suitable for once-weekly or once-monthly administration; for example, an insoluble salt of the active compound, such as the decanoate salt, may be adapted to provide a depot preparation for intramuscular injection. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a pharmaceutically acceptable salt thereof. When referring to these preformulation compositions as homogeneous, it is meant that the active ingredient is dispersed evenly throughout the composition so that the composition may be readily subdivided into equally effective dosage forms such as tablets, pills and capsules. This solid preformulation composition is then subdivided into unit dosage forms of the type described above containing from 0.1 to about 500 mg of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of material can be used for such enteric layers or coatings, such materials including a number of polymeric acids with such materials as shellac, cetyl alcohol and cellulose acetate.

The liquid forms in which the novel compositions of the present invention may be incorporated for administration orally or by injection include, aqueous solutions, suitably flavored syrups, aqueous or oil suspensions, and flavored emulsions with edible oils such as cottonseed oil, sesame oil, coconut oil or peanut oil, as well as elixirs and similar pharmaceutical vehicles. Suitable dispersing or suspending agents for aqueous suspensions, include synthetic and natural gums such as tragacanth, acacia, alginate, dextran, sodium carboxymethylcellulose, methylcellulose, polyvinyl-pyrrolidone or gelatin.

The method of treating a disorder mediated by one or more androgen receptor(s) described in the present invention may also be carried out using a pharmaceutical composition comprising any of the compounds as defined herein and a pharmaceutically acceptable carrier. The pharmaceutical composition may contain between about 0.1 mg and 500 mg, preferably about 50 to 100 mg, of the compound, and may be constituted into any form suitable for the mode of administration selected. Carriers include necessary and inert pharmaceutical excipients, including, but not limited to, binders, suspending agents, lubricants, flavorants, sweeteners, preservatives, dyes, and coatings. Compositions suitable for oral administration include solid forms, such as pills, tablets, caplets, capsules (each including immediate release, timed release and sustained release formulations), granules, and powders, and liquid forms, such as solutions, syrups, elixers, emulsions, and suspensions. Forms useful for parenteral administration include sterile solutions, emulsions and suspensions.

Advantageously, compounds of the present invention may be administered in a single daily dose, or the total daily dosage may be administered in divided doses of two, three or four times daily. Furthermore, compounds for the present invention can be administered in intranasal form via topical use of suitable intranasal vehicles, or via transdermal skin patches well known to those of ordinary skill in that art. To be administered in the form of a transdermal delivery system, the dosage administration will, of course, be continuous rather than intermittent throughout the dosage regimen.

For instance, for oral administration in the form of a tablet or capsule, the active drug component can be combined with an oral, non-toxic pharmaceutically acceptable inert carrier such as ethanol, glycerol, water and the like. Moreover, when desired or necessary, suitable binders; lubricants, disintegrating agents and coloring agents can also be incorporated into the mixture. Suitable binders include, without limitation, starch, gelatin, natural sugars such as glucose or beta-lactose, corn sweeteners, natural and synthetic gums such as acacia, tragacanth or sodium oleate, sodium stearate, magnesium stearate, sodium benzoate, sodium acetate, sodium chloride and the like. Disintegrators include, without limitation, starch, methyl cellulose, agar, bentonite, xanthan gum and the like.

The liquid forms in suitably flavored suspending or dispersing agents such as the synthetic and natural gums, for example, tragacanth, acacia, methyl-cellulose and the like. For parenteral administration, sterile suspensions and solutions are desired. Isotonic preparations which generally contain suitable preservatives are employed when intravenous administration is desired.

The compound of the present invention can also be administered in the form of liposome delivery systems, such as small unilamellar vesicles, large unilamellar vesicles, and multilamellar vesicles. Liposomes can be formed from a variety of phospholipids, such as cholesterol, stearylamine or phophatidylcholines.

Compounds of the present invention may also be delivered by the use of monoclonal antibodies as individual carriers to which the compound molecules are coupled. The compounds of the present invention may also be coupled with soluble polymers as targetable drug carriers. Such polymers can include polyvinylpyrrolidone, pyran copolymer, polyhydroxypropylmethacrylamidephenol, polyhydroxy-ethylaspartamidephenol, or polyethyl eneoxidepolylysine substituted with palmitoyl residue. Furthermore, the compounds of the present invention may be coupled to a class of biodegradable polymers useful in achieving controlled release of a drug, for example, polylactic acid, polyepsilon caprolactone, polyhydroxy butyeric acid, polyorthoesters, polyacetals, polydihydropyrans, polycyanoacrylates and cross-linked or amphipathic block copolymers of hydrogels.

Compounds of this invention may be administered in any of the foregoing compositions and according to dosage regimens established in the art whenever treatment of disorders mediated by one or more androgen receptor(s) is required.

The daily dosage of the products may be varied over a wide range from 0.01 to 1,000 mg per adult human per day. For oral administration, the compositions are preferably provided in the form of tablets containing, 0.01, 0.05, 0.1, 0.5, 1.0, 2.5, 5.0, 10.0, 15.0, 25.0, 50.0, 100, 150, 200, 250 and 500 milligrams of the active ingredient for the symptomatic adjustment of the dosage to the patient to be treated. An effective amount of the drug is ordinarily supplied at a dosage level of from about 0.01 mg/kg to about 300 mg/kg of body weight per day. Preferably, the range is from about 0.5 to about 5.0 mg/kg of body weight per day, most preferably, from about 1.0 to about 3.0 mg/kg of body weight per day. The compounds may be administered on a regimen of 1 to 4 times per day.

Optimal dosages to be administered may be readily determined by those skilled in the art, and will vary with the particular compound used, the mode of administration, the strength of the preparation, the mode of administration, and the advancement of the disease condition. In addition, factors associated with the particular patient being treated, including patient age, weight, diet and time of administration, will result in the need to adjust dosages.

The following Examples are set forth to aid in the understanding of the invention, and are not intended and should not be construed to limit in any way the invention set forth in the claims which follow thereafter.

In the Examples which follow, some synthesis products may be listed as having been isolated as a residue. It will be understood by one of ordinary skill in the art that the term "residue" does not limit the physical state in which the product was isolated and may include, for example, a solid, an oil, a foam, a gum, a syrup, and the like.

EXAMPLE 1

3-Methyl-5-trifluoromethyl-3,4-dihydro-2H-pyrazole-3-carbothioic acid (4-cyano-3-trifluoromethyl-phenyl)-amide

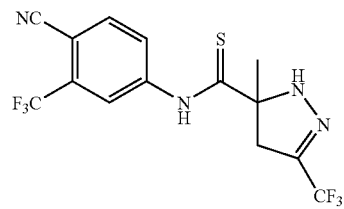

3-Methyl-5-trifluoromethyl-3,4-dihydro-2H-pyrazole-3-carboxylic acid (4-cyano-3-trifluoromethyl-phenyl)-amide (15 mmoL), disclosed in co-pending application Ser. No. 11/258,448 referenced above, Lawesson's agent (15 mmoL) in toluene (100 mL) was refluxed for 6 hrs until the solution turned clear. The reaction was cooled down and some precipitate was observed. The solid was removed by filtration and the filtrate was concentrated to give the crude product as a green oil, which was then purified by silica gel column chromatography using DCM and ethyl acetate as eluent to afford the title compound as a green solid.

$^1$H NMR (CDCl$_3$) δ 11.05 (s, 1H), 8.45 (s, 1H), 8.30 (d, J=8.5 Hz, 1H), 7.82 (d, J=8.5 Hz, 1H), 5.95 (br, s, 1H), 3.40 (abq, J=9.5 Hz, 1H), 3.21 (abq, J=9.5 Hz, 1H), 1.85 (s, 3H). MS (m/z): MH$^+$ 381.

EXAMPLE 2

N-(4-Cyano-3-trifluoromethyl-phenyl)-3-methyl-5-trifluoromethyl-3,4-dihydro-2H-pyrazole-3-carboximidothioic acid ethyl ester

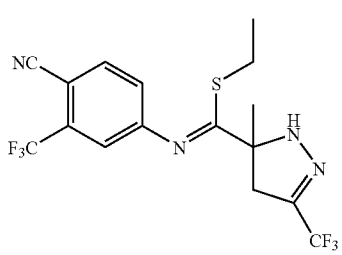

3-Methyl-5-trifluoromethyl-3,4-dihydro-2H-pyrazole-3-carbothioic acid (4-cyano-3-trifluoromethyl-phenyl)-amide (10 mmoL), K$_2$CO$_3$ (15 mmoL) in acetone was treated with EtI (10 mmoL) at room temperature. The reaction was slightly heated and stirred at 50° C. for 1 hr. The solid was filtrated and the filtrate was concentrated to give the crude product as a brown oil, which was then purified by silica gel column chromatography using hexanes and ethyl acetate as eluent to afford the title compound as a colorless oil.

$^1$H NMR (CDCl$_3$) δ 7.80 (d, J=7.8Hz, 1H), 7.28 (s, 1H), 7.15 (d, J=7.9 Hz, 1H), 6.50 (s, 1H), 3.51 (abq, J=12.5 Hz, 1H), 2.88 (abq, J=12.5 Hz, 1H), 2.35 (q, J=8.5 Hz, 2H), 1.08 (t, J=8.5 Hz, 3H). MS (m/z): MH$^+$ 409.

EXAMPLE 3

4-(6-Amino-3a-methyl-2-trifluoromethyl-3,3a-dihydro-imidazo[1,5-b]pyrazol-4-ylideneamino)-2-trifluoromethyl-benzonitrile Compound 1

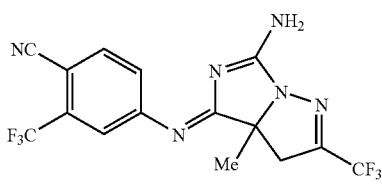

N-(4-Cyano-3-trifluoromethyl-phenyl)-3-methyl-5-trifluoromethyl-3,4-dihydro-2H-pyrazole-3-carboximidothioic acid ethyl ester (4.2 mmoL) in dioxane (20 mL) was treated with NH$_2$CN (6.25 mmoL) and K$_2$CO$_3$ (8.40 mmoL). The reaction mixture was heated to 100° C. for 30 min. The solid was filtered off and the filtrate was then concentrated to give yellow solid, which was then purified by flash column chromatography using hexanes and ethyl acetate (4:1 to 1:1) as eluent to afford the title compound as a white solid.

$^1$H NMR (CDCl$_3$) δ 7.75 (b, s, 1H), 7.70 (d, J=8.0 Hz, 1H), 7.38 (s, 1H), 7.23 (d, J=8.0 Hz, 1H), 5.65 (br, s, 1H), 3.45 (abq, J=10.5 Hz, 1H), 2.98 (abq, J=10.5 Hz, 1H), 1.61 (s, 3H). MS (m/z): MH$^+$ 389.

EXAMPLE 4

3R-Methyl-5-trifluoromethyl-3,4-dihydro-2H-pyrazole-3-carbothioic acid (4-cyano-3-trifluoromethyl-phenyl)-amide

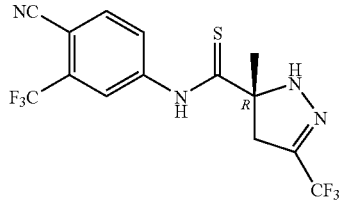

Follow the procedure in Example 1, using 3R-methyl-5-trifluoromethyl-3,4-dihydro-2H-pyrazole-3-carboxylic acid (4-cyano-3-trifluoromethyl-phenyl)-amide as starting material, disclosed in co-pending application Ser. No. 11/258,448 referenced above, yield the title compound as a yellow solid. NMR and MS data are the same as that of Example 1.

EXAMPLE 5

N-(4-Cyano-3-trifluoromethyl-phenyl)-3R-methyl-5-trifluoromethyl-3,4-dihydro-2H-pyrazole-3-carboximidothioic acid ethyl ester

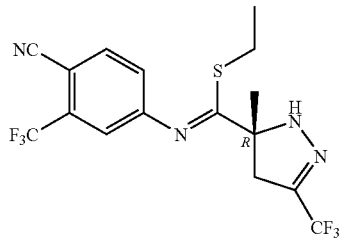

Follow the procedure in Example 2, using as 3R-methyl-5-trifluoromethyl-3,4-dihydro-2H-pyrazole-3-carbothioic acid (4-cyano-3-trifluoromethyl-phenyl)-amide as starting material, disclosed in co-pending application Ser. No. 11/258,448, yield the title compound as a colorless oil. NMR and MS data are the same as that of Example 2.

EXAMPLE 6

4-(6-Amino-3aR-methyl-2-trifluoromethyl-3,3a-dihydro-imidazo[1,5-b]pyrazol-4-ylideneamino)-2-trifluoromethyl-benzonitrile Compound 2

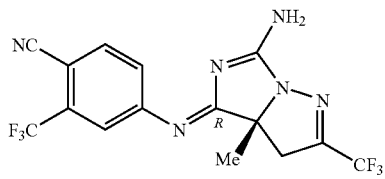

Follow the procedure in Example 3, using N-(4-cyano-3-trifluoromethyl-phenyl)-3R-methyl-5-trifluoromethyl-3,4-dihydro-2H-pyrazole-3-carboximidothioic acid ethyl ester as starting material yield the title compound as a white solid. NMR and MS data are the same as that of Example 3. [α]$^{20}_{MeOH}$ –313.8 (c 0.33).

EXAMPLE 7

3S-Methyl-5-trifluoromethyl-3,4-dihydro-2H-pyrazole-3-carbothioic acid (4-cyano-3-trifluoromethyl-phenyl)-amide

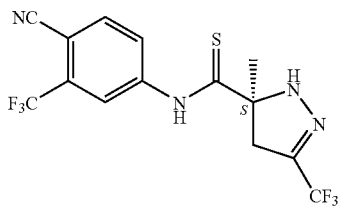

Follow the procedure in Example 1, using 3S-methyl-5-trifluoromethyl-3,4-dihydro-2H-pyrazole-3-carboxylic acid (4-cyano-3-trifluoromethyl-phenyl)-amide as starting material, disclosed in co-pending application Ser. No. 11/258,448 referenced above, yield the title compound as a yellow solid. NMR and MS data are the same as that of Example 1.

EXAMPLE 8

N-(4-Cyano-3-trifluoromethyl-phenyl)-3S-methyl-5-trifluoromethyl-3,4-dihydro-2H-pyrazole-3-carboximidothioic acid ethyl ester

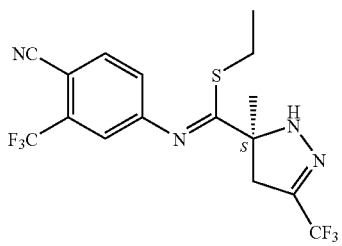

Follow the procedure in Example 2, using as 3S-methyl-5-trifluoromethyl-3,4-dihydro-2H-pyrazole-3-carbothioic acid (4-cyano-3-trifluoromethyl-phenyl)-amide as starting material, disclosed in co-pending application Ser. No. 11/258,448 referenced above, yield the title compound as a colorless oil. NMR and MS data are the same as that of Example 2.

EXAMPLE 9

4-(6-Amino-3aS-methyl-2-trifluoromethyl-3,3a-dihydro-imidazo[1,5-b]pyrazol-4-ylideneamino)-2-trifluoromethyl-benzonitrile Compound 3

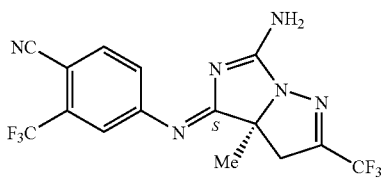

Follow the procedure in Example 3, using N-(4-cyano-3-trifluoromethyl-phenyl)-3S-methyl-5-trifluoromethyl-3,4-dihydro-2H-pyrazole-3-carboximidothioic acid ethyl ester as starting material yield the title compound as a white solid. NMR and MS data are the same as that of Example 3. $[\alpha]^{20}_{MeOH}$+356.2 (c 0.45).

EXAMPLE 10

3-Methyl-5-trifluoromethyl-3,4-dihydro-2H-pyrazole-3-carbothioic acid (3,4-dichloro-phenyl)-amide

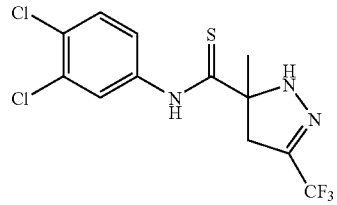

Follow the procedure in Example 1, using 3-methyl-5-trifluoromethyl-3,4-dihydro-2H-pyrazole-3-carboxylic acid (3,4-dichloro-phenyl)-amide as starting material, disclosed in co-pending application Ser. No. 11/258,448 referenced above, yield the title compound as a yellow solid.
$^1$H NMR (CDCl$_3$) δ 10.70 (s, 1H), 8.10 (s, 1H), 7.65 (m, 1H), 7.45 (m, 1H), 5.80 (s, 1H), 3.30 and 3.15 (abq, J=13.0 Hz, 2H), 1.80 (s, 3H). MS (m/z): MH$^+$ 357.

EXAMPLE 11

N-(3,4-Dichloro-phenyl)-3-methyl-5-trifluoromethyl-3,4-dihydro-2H-pyrazole-3-carboximidothioic acid ethyl ester

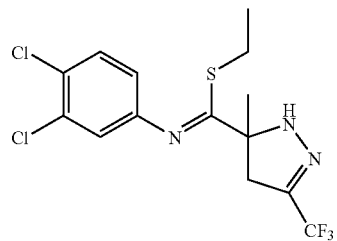

Follow the procedure in Example 2, using 3-methyl-5-trifluoromethyl-3,4-dihydro-2H-pyrazole-3-carbothioic acid (3,4-dichloro-phenyl)-amide as starting material to yield the title compound as a colorless oil.
$^1$H NMR (CDCl$_3$) δ 7.40 (m, 1H), 7.00 (s, 1H), 6.80 (m, 1H), 6.60 (br, 1H), 5.30 (s, 1H), 3.50 and 2.80 (abq, J=14.0 Hz, 2H), 2.30 (m, 2H), 1.60 (s, 3H), 1.00 (m, 3H). MS (m/z): MH$^+$ 385.

EXAMPLE 12

4-(3,4-Dichloro-phenylimino)-3a-methyl-2-trifluoromethyl-3a,4-dihydro-3H-imidazo[1,5-b]pyrazol-6-ylamine Compound 4

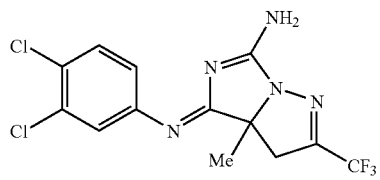

Follow the procedure in Example 3, using N-(3,4-Dichloro-phenyl)-3-methyl-5-trifluoromethyl-3,4-dihydro-2H-pyrazole-3-carboximidothioic acid ethyl ester as starting material yield the title compound as a white solid.
$^1$H NMR (CDCl$_3$) δ 8.30 (br, s, 1H), 7.36 (d, J=8.5 Hz, 1H), 7.08 (s, 1H), 6.82 (d, J=8.5 Hz, 1H), 5.10 (br, s, 1H), 3.45 (abq, J=11.0 Hz, 1H), 2.95 (abq, J=11.0 Hz, 1H), 1.61 (s, 3H). MS (m/z): MH$^+$ 364.

EXAMPLE 13

3-Methyl-5-trifluoromethyl-3,4-dihydro-2H-pyrazole-3-carbothioic acid (4-nitro-3-trifluoromethyl-phenyl)-amide

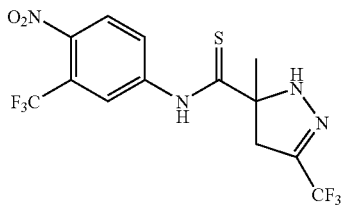

Follow the procedure in Example 1, using 3-methyl-5-trifluoromethyl-3,4-dihydro-2H-pyrazole-3-carboxylic acid (4-nitro-3-trifluoromethyl-phenyl)-amide as starting material, disclosed in co-pending application Ser. No. 11/258,448, yield the title compound as a yellow solid.

$^1$H NMR (CDCl$_3$) δ 8.45 (s, 1H), 8.40 (d, J=8.6 Hz, 1H), 7.98 (d, J=8.0 Hz, 1H), 6.01 (br, s, 1H), 3.30 (abq, J=10.5 Hz, 2H), 1.82 (s, 3H). MS (m/z): MH$^+$ 401.

EXAMPLE 14

3-Methyl-N-(4-nitro-3-trifluoromethyl-phenyl)-5-trifluoromethyl-3,4-dihydro-2H-pyrazole-3-carboximidothioic acid ethyl ester

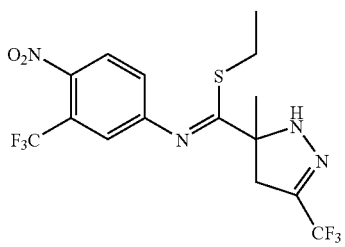

Follow the procedure in Example 2, using 3-methyl-5-trifluoromethyl-3,4-dihydro-2H-pyrazole-3-carbothioic acid (4-nitro-3-trifluoromethyl-phenyl)-amide as starting material to yield the title compound as a colorless oil.

$^1$H NMR (CDCl$_3$) δ 7.98 (d, J=8.0 Hz, 1H), 7.32 (s, 1H), 7.18 (d, J=7.5 Hz, 1H), 6.45 (br, s, 1H), 3.51 (abq, J=14.5 Hz, 1H), 2.85 (abq, J=14.5 Hz, 1H), 2.35 (q, J=7.8 Hz, 2H), 1.68 (s, 3H), 1.09 (t, J=8.5 Hz, 3H). MS (m/z): MH$^+$ 429.

EXAMPLE 15

3a-Methyl-4-(4-nitro-3-trifluoromethyl-phenylimino)-2-trifluoromethyl-3a,4-dihydro-3H-imidazo[1,5-b]pyrazol-6-ylamine Compound 5

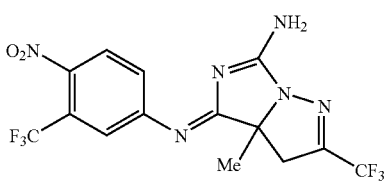

Follow the procedure in Example 3, using 3-methyl-N-(4-nitro-3-trifluoromethyl-phenyl)-5-trifluoromethyl-3,4-dihydro-2H-pyrazole-3-carboximidothioic acid ethyl ester as starting material yield the title compound as a white solid.

$^1$H NMR (CDCl$_3$) δ 8.15 (br, s, 1H), 7.55 (d, J=7.5 Hz, 1H), 7.10 (s, 1H), 6.79 (d, J=8.0 Hz, 1H), 5.45 (br, s, 1H), 3.50 (abq, J=12.5 Hz, 1H), 3.00 (abq, J=12.5 Hz, 1H), 1.65 (s, 3H). MS (m/z): MH$^+$ 409.

EXAMPLE 16

3-Methyl-3,4-dihydro-2H-pyrazole-3-carbothioic acid (4-cyano-3-trifluoromethyl-phenyl)-amide

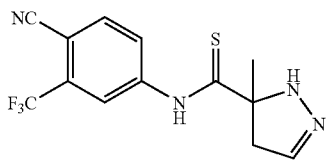

Follow the procedure in Example 1, using 3-methyl-3,4-dihydro-2H-pyrazole-3-carboxylic acid (4-cyano-3-trifluoromethyl-phenyl)-amide as starting material, disclosed in co-pending application Ser. No. 11/258,448, yield the title compound as a yellow solid.

$^1$H NMR (CDCl$_3$) δ 8.52 (s, 1H), 8.45 (d, J=7.8 Hz, 1H), 7.88 (d, J=8.5 Hz, 1H), 6.88 (s, 1H), 5.50 (br, s, 1H), 3.15 (abq, J=12.5 Hz, 2H), 1.76 (s, 3H). MS (m/z): MH$^+$ 313.

EXAMPLE 17

N-(4-Cyano-3-trifluoromethyl-phenyl)-3-methyl-3,4-dihydro-2H-pyrazole-3-carboximidothioic acid ethyl ester

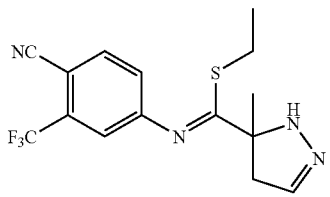

Follow the procedure in Example 2, using 3-methyl-3,4-dihydro-2H-pyrazole-3-carbothioic acid (4-cyano-3-trifluoromethyl-phenyl)-amide as starting material to yield the title compound as a colorless oil.

$^1$H NMR (CDCl$_3$) δ 7.75 (d, J=8.0 Hz, 1H), 7.25 (s, 1H), 7.10 (d, J=8.0 Hz, 1H), 6.75 (s, 1H), 5.96 (br, s, 1H), 3.25 (abq, J=10.5 Hz, 1H), 2.68 (abq, J=10.5 Hz, 1H), 2.40 (q, J=8.6 Hz, 2H), 1.52 9s, 3H), 1.08 (t, J=8.5 Hz, 3H). MS (m/z): MH$^+$ 341.

EXAMPLE 18

4-(6-Amino-3a-methyl-3,3a-dihydro-imidazo[1,5-b]pyrazol-4-ylideneamino)-2-trifluoromethyl-benzonitrile Compound 6

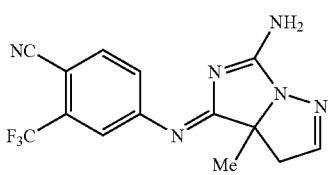

Follow the procedure in Example 3, using N-(4-cyano-3-trifluoromethyl-phenyl)-3-methyl-3,4-dihydro-2H-pyrazole-3-carboximidothioic acid ethyl ester as starting material yield the title compound as a white solid.

$^1$H NMR (MeOD) δ 7.82 (d, J=8.5 Hz, 1H), 7.62 (s, 1H), 7.48 (d, J=8.0 Hz, 1H), 7.25 (s, 1H), 3.25 (abq, J=12.5 Hz, 1H), 2.72 (abq, J=12.5 Hz, 1H0, 1.52 (s, 3H). MS (m/z): MH$^+$ 321.

EXAMPLE 19

5-(4-Cyano-3-trifluoromethyl-phenylthiocarbamoyl)-5-methyl-4,5-dihydro-1H-pyrazole-3-carboxylic acid ethyl ester

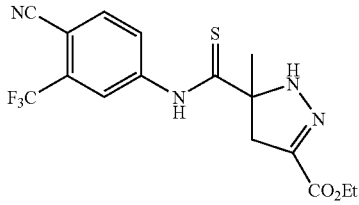

Follow the procedure in Example 1, using 5-(4-cyano-3-trifluoromethyl-phenylcarbamoyl)-5-methyl-4,5-dihydro-1H-pyrazole-3-carboxylic acid ethyl ester as starting material, disclosed in co-pending application Ser. No. 11/258,448, yield the title compound as a yellow solid.

$^1$H NMR (CDCl$_3$) δ 11.01 (br, s, 1H), 8.45 (s, 1H), 8.40 (d, J=7.0 Hz, 1H), 7.85 (d, J=7.0 Hz, 1H), 4.30 (q, J=6.5 Hz, 2H), 3.32 (abq, J=12.0 Hz, 2H), 1.78 (s, 3H), 1.38 (t, J=8.0 Hz, 3H). MS (m/z): MH$^+$ 385.

EXAMPLE 20

5-[(4-Cyano-3-trifluoromethyl-phenylimino)-ethylsulfanyl-methyl]-5-methyl-4,5-dihydro-1H-pyrazole-3-carboxylic acid ethyl ester

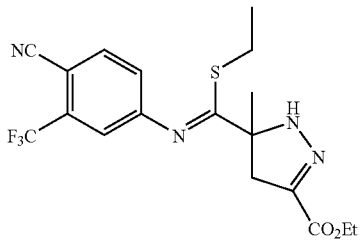

Follow the procedure in Example 2, using 5-(4-cyano-3-trifluoromethyl-phenylthiocarbamoyl)-5-methyl-4,5-dihydro-1H-pyrazole-3-carboxylic acid ethyl ester as starting material to yield the title compound as a colorless oil.

$^1$H NMR (CDCl$_3$) δ 7.78 (d, J=8.5Hz, 1H), 7.25 (s, 1H), 7.10 (d, J=8.0 Hz, 1H), 6.62 (br, s, 1H), 4.35 (q, J=6.0 Hz, 2H), 3.51 (abq, J=13.0 Hz, 1H), 2.90 (abq, J=13.0 Hz, 1H), 2.88 (q, J=6.0 Hz, 2H), 1.59 (s, 3H), 1.38 (t, J=7.5 Hz, 3H), 1.10 (t, J=8.0 Hz, 3H). MS (m/z): MH$^+$ 413.

EXAMPLE 21

6-Amino-4-(4-cyano-3-trifluoromethyl-phenylimino)-3a-methyl-3a,4-dihydro-3H-imidazo[1,5-b]pyrazole-2-carboxylic acid ethyl ester Compound 7

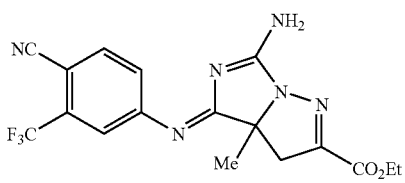

Follow the procedure in Example 3, using 5-[(4-cyano-3-trifluoromethyl-phenylimino)-ethylsulfanyl-methyl]-5-methyl-4,5-dihydro-1H-pyrazole-3-carboxylic acid ethyl ester as starting material yield the title compound as a white solid.

$^1$H NMR (CDCl$_3$) δ 7.71 (d, J=7.5 Hz, 1H), 7.41 (s, 1H), 7.25 (d, J=7.5 Hz, 1H), 7.08 (br, s, 1H), 6.10 (br, s, 1H), 4.40 (q, J=7.0 Hz, 2H), 3.50 (abq, J=12.5 Hz, 1H), 3.06 (abq, J=12.5 Hz, 1H), 1.61 (s, 3H), 1.38 (t, J=8.0 Hz, 3H). MS (m/z): MH$^+$ 393.

EXAMPLE 22

3-Ethyl-5-trifluoromethyl-3,4-dihydro-2H-pyrazole-3-carbothioic acid (4-cyano-3-trifluoromethyl-phenyl)-amide

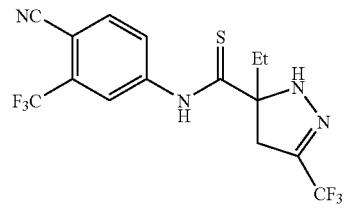

Follow the procedure in Example 1, using 3-ethyl-5-trifluoromethyl-3,4-dihydro-2H-pyrazole-3-carboxylic acid (4-cyano-3-trifluoromethyl-phenyl)-amide as starting material, disclosed in co-pending application Ser. No. 11/258,448 referenced above, yield the title compound as a yellow solid.

$^1$H NMR (CDCl$_3$) δ 8.48 (s, 1H), 8.40 (d, J=7.5 Hz, 1H), 7.88 (d, J=8.0 Hz, 1H), 6.21 (br, s, 1H), 3.42 (abq, J=12.5 Hz, 1H), 3.35 (abq, J=12.5 Hz, 1H), 2.40 9m, 1H), 2.25 (m, 1H), 0.98 (t, J=9.0 Hz, 3H). MS (m/z): MH$^+$ 395.

EXAMPLE 23

N-(4-Cyano-3-trifluoromethyl-phenyl)-3-ethyl-5-trifluoromethyl-3,4-dihydro-2H-pyrazole-3-carboximidothioic acid ethyl ester

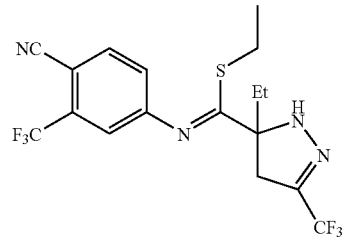

Follow the procedure in Example 2, using 3-ethyl-5-trifluoromethyl-3,4-dihydro-2H-pyrazole-3-carbothioic acid (4-cyano-3-trifluoromethyl-phenyl)-amide as starting material to yield the title compound as a colorless oil.

$^1$H NMR (CDCl$_3$) δ 7.78 (d, J=8.5Hz, 1H), 7.25 (s, 1H), 7.12 (d, J=8.5 Hz, 1H), 6.62 (br, s, 1H), 3.52 (abq, J=14.0 Hz, 1H), 2.93 (d, J=14.0 Hz, 1H), 2.30 (q, J=9.0 Hz, 2H), 2.05 (m, 2H), 1.10 (t, J=9.0 Hz, 3H), 1.05 (t, J=8.5 Hz, 3H). MS (m/z): MH$^+$ 423.

EXAMPLE 24

4-(6-Amino-3a-ethyl-2-trifluoromethyl-3,3a-dihydro-imidazo[1,5-b]pyrazol-4-ylideneamino)-2-trifluoromethyl-benzonitrile Compound 8

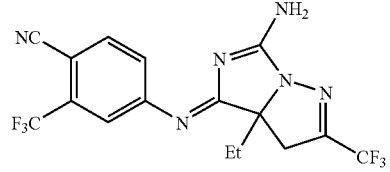

Follow the procedure in Example 3, using N-(4-cyano-3-trifluoromethyl-phenyl)-3-ethyl-5-trifluoromethyl-3,4-dihydro-2H-pyrazole-3-carboximidothioic acid ethyl ester as starting material yield the title compound as a white solid.

$^1$H NMR (CDCl$_3$) δ 7.75 (d, J=7.5 Hz, 1H), 7.42 (s, 1H), 7.24 (d, J=7.5 Hz, 1H), 3.45 (abq, J=14.0 Hz, 1H), 3.04 (abq, J=14.0 Hz, 1H), 1.95 (m, 1H), 1.90 (m, 1H), 1.02 (t, J=8.5 Hz, 3H). MS (m/z): MH+ 403.

EXAMPLE 25

3-Methyl-5-trifluoromethyl-3,4-dihydro-2H-pyrazole-3-carbothioic acid (4-cyano-2-ethyl-3-trifluoromethyl-phenyl)-amide

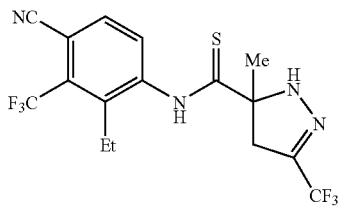

Follow the procedure in Example 1, using 3-methyl-5-trifluoromethyl-3,4-dihydro-2H-pyrazole-3-carboxylic acid (4-cyano-2-ethyl-3-trifluoromethyl-phenyl)-amide as starting material, disclosed in co-pending application Ser. No. 11/258,448, yield the title compound as a yellow solid.

$^1$H NMR (CDCl$_3$) δ 10.91 (br, s, 1H), 8.48 (d, J=8.5 Hz, 1H), 7.75 (d, J=8.5 Hz, 1H), 6.08 (br, s, 1H), 3.40 (abq, J=13.5 Hz, 1H), 3.28 (abq, J=13.5 Hz, 1H), 2.80 (q, J=6.0 Hz, 2H), 1.86 (s, 3H), 1.21 (t, J=8.0 Hz, 3H). MS (m/z): MH+ 409.

EXAMPLE 26

N-(4-Cyano-2-ethyl-3-trifluoromethyl-phenyl)-3-methyl-5-trifluoromethyl-3,4-dihydro-2H-pyrazole-3-carboximidothioic acid ethyl ester

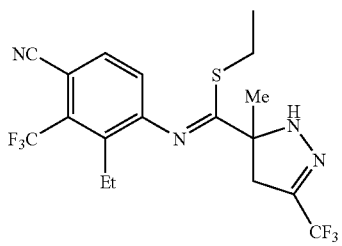

Follow the procedure in Example 2, using 3-methyl-5-trifluoromethyl-3,4-dihydro-2H-pyrazole-3-carbothioic acid (4-cyano-2-ethyl-3-trifluoromethyl-phenyl)-amide as starting material to yield the title compound as a colorless oil.

$^1$H NMR (CDCl$_3$) δ 7.61 (d, J=8.0 Hz, 1H), 7.05 (d, J=8.0 Hz, 1H), 6.58 (br, s, 1H), 3.55 (abq, J=13.0 Hz, 1H), 2.95 (abq, J=13.0 Hz, 1H), 2.70 (q, J=7.0 Hz, 2H), 2.35 (m, 2H), 1.68 (s, 3H), 1.12 (t, J=8.5 Hz, 3H), 1.09 (t, J=8.0 Hz, 3H). MS (m/z): MH+ 437.

EXAMPLE 27

4-(6-Amino-3a-methyl-2-trifluoromethyl-3,3a-dihydro-imidazo[1,5-b]pyrazol-4-ylideneamino)-3-ethyl-2-trifluoromethyl-benzonitrile Compound 9

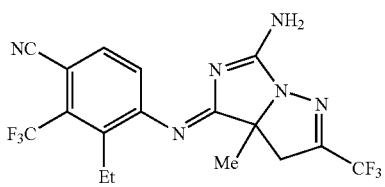

Follow the procedure in Example 3, using N-(4-cyano-2-ethyl-3-trifluoromethyl-phenyl)-3-methyl-5-trifluoromethyl-3,4-dihydro-2H-pyrazole-3-carboximidothioic acid ethyl ester as starting material yield the title compound as a white solid.

$^1$H NMR (CDCl$_3$) δ 7.61 (d, J=8.5 Hz, 1H), 7.10 (br, s, 1H), 7.06 (d, J=8.5 Hz, 1H), 5.38 (br, s, 1H), 3.45 (abq, J=12.5 Hz, 1H), 3.05 (abq, J=12.5 Hz, 1H), 2.75 (q, J=6.0 Hz, 2H), 1.68 (s, 3H), 1.06 (t, J=7.5 Hz, 3H). MS (m/z): MH+ 417.

EXAMPLE 28

3-Methyl-5-trifluoromethyl-3,4-dihydro-2H-pyrazole-3-carbothioic acid (4-bromo-3-trifluoromethyl-phenyl)-amide

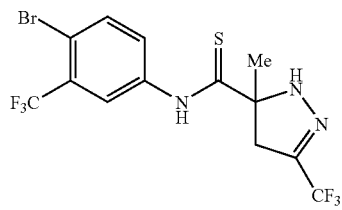

Follow the procedure in Example 1, using 3-methyl-5-trifluoromethyl-3,4-dihydro-2H-pyrazole-3-carboxylic acid (4-bromo-3-trifluoromethyl-phenyl)-amide as starting material, disclosed in co-pending application Ser. No. 11/258,448, yield the title compound as a yellow solid.

$^1$H NMR (CDCl$_3$) δ 10.78 (br, s, 1H), 8.21 (s, 1H), 8.02 (d, J=8.5 Hz, 1H), 7.74 (d, J=7.5 Hz, 1H), 5.90 (br, s, 1H), 3.25 (abq, J=14.0 Hz, 2H), 1.82 (s, 3H). MS (m/z): MH+ 434.

EXAMPLE 29

N-(4-Bromo-3-trifluoromethyl-phenyl)-3-methyl-5-trifluoromethyl-3,4-dihydro-2H-pyrazole-3-carboximidothioic acid ethyl ester

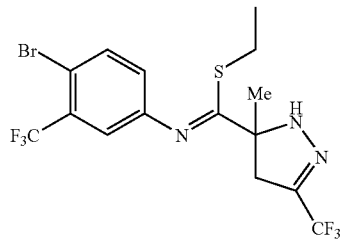

Follow the procedure in Example 2, using 3-methyl-5-trifluoromethyl-3,4-dihydro-2H-pyrazole-3-carbothioic acid (4-bromo-3-trifluoromethyl-phenyl)-amide as starting material to yield the title compound as a colorless oil.

$^1$H NMR (CDCl$_3$) δ 7.65 (d, J=8.0 Hz, 1H), 7.25 (s, 1H), 6.95 (d, J=8.0 Hz, 1H), 6.62 (br, s, 1H), 3.55 (abq, J=10.5 Hz, 1H), 2.83 (abq, J=10.5 Hz, 1H), 2.36 (m, 2H), 1.62 (s, 3H), 1.06 (t, J=8.0 Hz, 3H). MS (m/z): MH+ 462.

EXAMPLE 30

4-(4-Bromo-3-trifluoromethyl-phenylimino)-3a-methyl-2-trifluoromethyl-3a,4-dihydro-3H-imidazo[1,5-b]pyrazol-6-ylamine Compound 10

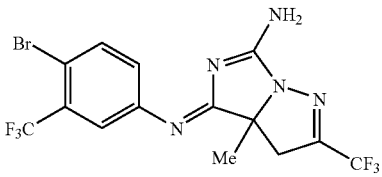

Follow the procedure in Example 3, using N-(4-bromo-3-trifluoromethyl-phenyl)-3-methyl-5-trifluoromethyl-3,4-dihydro-2H-pyrazole-3-carboximidothioic acid ethyl ester as starting material yield the title compound as a white solid.

$^1$H NMR (CDCl$_3$) δ 8.18 (br, s, 1H), 7.61 (d, J=7.5 Hz, 1H), 7.31 (s, 1H), 7.01 (d, J=8.0 Hz, 1H), 5.23 (br, s, 1H), 3.42 (abq, J=13.5 Hz, 1H), 2.95 (abq, J=13.5 Hz, 1H), 1.62 (s, 3H). MS (m/z): MH$^+$ 442.

EXAMPLE 31

3-Methyl-5-pentafluorophenyl-3,4-dihydro-2H-pyrazole-3-carbothioic acid (4-cyano-3-trifluoromethyl-phenyl)-amide

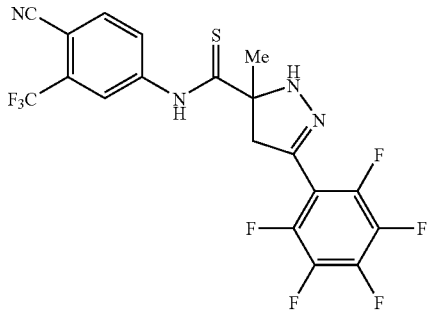

Follow the procedure in Example 1, using 3-methyl-5-pentafluorophenyl-3,4-dihydro-2H-pyrazole-3-carboxylic acid (4-cyano-3-trifluoromethyl-phenyl)-amide as starting material, disclosed in co-pending application Ser. No. 11/258,448 referenced above, yield the title compound as a yellow solid.

$^1$H NMR (CDCl$_3$) δ 8.45 (s, 1H), 8.40 (d, J=7.5 Hz, 1H), 7.85 (d, J=8.0 Hz, 1H), 5.96 (br, s, 1H), 3.52 (abq, J=11.5 Hz, 2H), 1.88 (s, 3H). MS (m/z): MH$^+$ 479.

EXAMPLE 32

N-(4-Cyano-3-trifluoromethyl-phenyl)-3-methyl-5-pentafluorophenyl-3,4-dihydro-2H-pyrazole-3-carboximidothioic acid ethyl ester

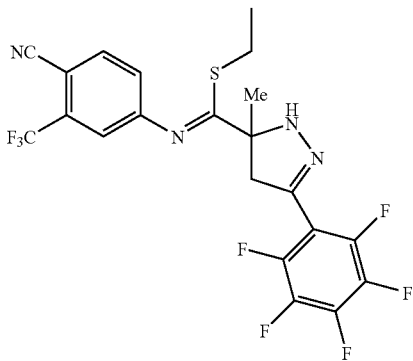

Follow the procedure in Example 2, using 3-methyl-5-pentafluorophenyl-3,4-dihydro-2H-pyrazole-3-carbothioic acid (4-cyano-3-trifluoromethyl-phenyl)-amide as starting material to yield the title compound as a colorless oil.

$^1$H NMR (CDCl$_3$) δ 7.78 (d, J=8.5Hz, 1H), 7.28 (s, 1H), 7.12 (d, J=8.0 Hz, 1H), 6.55 (br, s, 1H), 3.60 (abq, J=12.0 Hz, 1H), 3.05 (abq, J=12.0 Hz, 1H), 2.38 (q, J=8.5 Hz, 2H), 1.65 (s, 3H), 1.10 (t, J=8.5 Hz, 3H). MS (m/z): MH$^+$ 507.

EXAMPLE 33

4-(6-Amino-3a-methyl-2-pentafluorophenyl-3,3a-dihydro-imidazo[1,5-b]pyrazol-4-ylideneamino)-2-trifluoromethyl-benzonitrile Compound 11

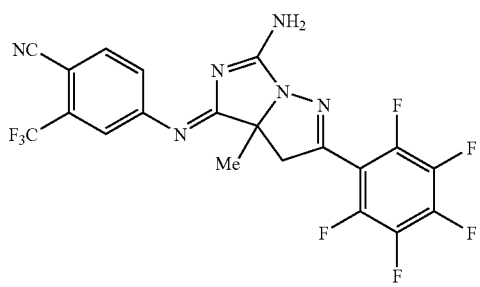

Follow the procedure in Example 3, using N-(4-cyano-3-trifluoromethyl-phenyl)-3-methyl-5-pentafluorophenyl-3,4-dihydro-2H-pyrazole-3-carboximidothioic acid ethyl ester as starting material yield the title compound as a white solid.

$^1$H NMR (MeOD) δ 7.88 (d, J=7.5 Hz, 1H), 7.75 (s, 1H), 7.55 (d, J=7.8 Hz, 1H), 3.21 (abq, J=10.5 Hz, 1H), 2.61 (abq, J=10.5 Hz, 1H), 1.61 (s, 3H). MS (m/z): MH$^+$ 487.

EXAMPLE 34

N-[4-(4-Cyano-3-trifluoromethyl-phenylimino)-3aS-methyl-2-trifluoromethyl-3a,4-dihydro-3H-imidazo[1,5-b]pyrazol-6-yl]-3,3,3-trifluoro-2R-methoxy-2-phenyl-propionamide Compound 12

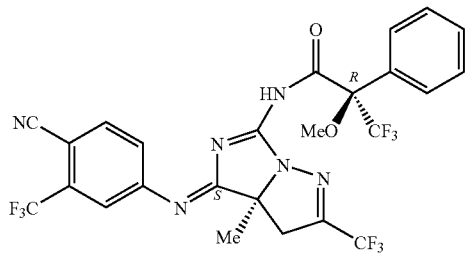

4-(6-Amino-3aS-methyl-2-trifluoromethyl-3,3a-dihydro-imidazo[1,5-b]pyrazol-4-ylideneamino)-2-trifluoromethyl-benzonitrile (0.80 mmoL) in DCM (5 mL) was treated with pyridine (1.2 mmoL) followed by (R)-Mosher's chloride (0.80 mmoL) at 0° C. The reaction was gradually warmed to room temperature over 4 hrs. The reaction mixture was then partitioned between DCM and sat NaHCO$_3$. The organic layer was washed with brine, dried over anhydrous Na$_2$SO$_4$, filtered and concentrated to afford the crude material, which was then purified by flash column chromatography using hexanes: ethyl acetate 4:1 to pure ethyl acetate as eluent to afford the title compound as a white solid.

$^1$H NMR (CDCl$_3$) δ 9.31 (br, s, 1H), 7.75 (d, J=7.5 Hz, 1H), 7.55 (m, 3H), 7.45 (m, 4H), 3.58 (s, 3H), 3.53 (abq, J=12.5 Hz, 1H), 3.12 (abq, J=12.5 z, 1H), 1.71 (s, 3H). MS (m/z): MH$^+$ 637.

EXAMPLE 35

N-[4-(4-Cyano-3-trifluoromethyl-phenylimino)-3aR-methyl-2-trifluoromethyl-3a,4-dihydro-3H-imidazo[1,5-b]pyrazol-6-yl]-2,2,2-trifluoro-acetamide Compound 13

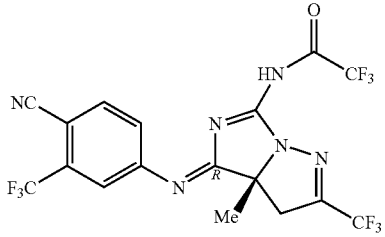

4-(6-Amino-3aR-methyl-2-trifluoromethyl-3,3a-dihydro-imidazo[1,5-b]pyrazol-4-ylideneamino)-2-trifluoromethyl-benzonitrile (1.2 mmoL) in DCM (6 mL) was treated with triethyl amine (2.5 mmoL) followed by trifluoroacetic anhydride (1.2 mmoL) at 0° C. The reaction was gradually warmed to room temperature over 2 hrs. The reaction mixture was then partitioned between DCM and sat NaHCO$_3$. The organic layer was washed with brine, dried over anhydrous Na$_2$SO$_4$, filtered and concentrated to afford the crude material, which was then purified by flash column chromatography using hexanes: ethyl acetate 6:1 to 1:1 as eluent to afford the title compound as a white solid.

$^1$H NMR (CDCl$_3$) δ 7.85 (d, J=7.0 Hz, 1H), 7.35 (s, 1H), 7.20 (m, 1H), 3.60 (abq, J=10.5 Hz, 1H), 3.15 (abq, J=10.5 Hz, 1H), 1.78 (s, 1H). MS (m/z): MH$^+$ 485.

EXAMPLE 36

1-[4-(4-Cyano-3-trifluoromethyl-phenylimino)-3aR-methyl-2-trifluoromethyl-3a,4-dihydro-3H-imidazo[1,5-b]pyrazol-6-yl]-3-(4-iodo-phenyl)-urea Compound 14

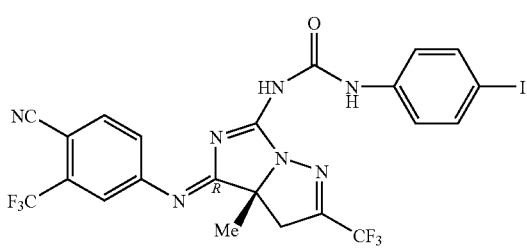

4-(6-Amino-3a R-methyl-2-trifluoromethyl-3,3a-dihydro-imidazo[1,5-b]pyrazol-4-ylideneamino)-2-trifluoromethyl-benzonitrile (3.4 mmoL), 4-iodo-phenylisocynate (3.2 mmoL) in dioxane (10 mL) was heated to 100° C. for 1 h. The solvent was removed and the residue was purified by flash column chromatography using hexanes: ethyl acetate 6:1 to 1:1 as eluent to afford the title compound as a white solid.

$^1$H NMR (CDCl$_3$) δ 10.35 (s, 1H), 7.82 (d, J=7.0 Hz, 1H), 7.58 (d, J=8.5 Hz, 2H), 7.52 (s, 1H), 7.35 (d, J=7.5 Hz, 1H), 6.89 (d, J=8.5 Hz, 1H), 3.55 (abq, J=11.5 Hz, 1H), 3.12 (abq, J=11.5 Hz, 1H), 1.72 (s, 3H). MS (m/z): MH$^+$ 634.

EXAMPLE 37

4-(6-Amino-3aR-methyl-2-trifluoromethyl-3,3a-dihydro-imidazo[1,5-b]pyrazol-4-ylideneamino)-2-trifluoromethyl-benzonitrile-Hydrates

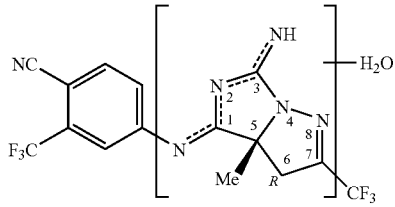

Hydrate 1 (Compound 16), Hydrate 2 (Compound 17) and Hydrate 3 (Compound 20)

4-(6-Amino-3aR-methyl-2-trifluoromethyl-3,3a-dihydro-imidazo[1,5-b]pyrazol-4-ylideneamino)-2-trifluoromethyl-benzonitrile (1.5 mmoL) in THF (5 mL) and HCl (1 N, 5 mL) was stirred at room temperature for 24 hrs. The solvent was removed and the residue was partitioned between ethyl acetate and sat. NaHCO$_3$ aq. solution. The organic layer was washed with water and brine, dried over anhydrous Na$_2$SO$_4$, filtered and concentrated to afford the crude materials. NMR showed 8:1:1 ratio of hydrate 1:hydrate 2:hydrate 3. The crude materials were separated by flash column chromatography using hexanes: ethyl acetate 1:1 to pure ethyl acetate (0.5% Et$_3$N added) as eluent to afford the title compounds as white solids.

Hydrate 1:
$^1$H NMR (CDCl$_3$) δ 8.02 (s, 1H), 7.90 (d, J=7.5 Hz, 1H), 7.72 (d, J=7.5 Hz, 1H), 5.55 (br, s, 1H), 5.22 (br, s, 1H), 4.38 (d, J=12.0Hz, 1H), 3.02 (d, J=12.0 Hz, 1H), 1.98 (s, 3H). MS (m/z): MH$^+$ 407.

Hydrate 2 JNJ:
$^1$H NMR (CDCl$_3$) δ 7.75 (d, J=8.0 Hz, 1H), 7.22 (s, 1H), 7.10 (d, J=7.5 Hz, 1H), 6.10 (br, s, 2H), 4.50 (d, J=12.5 Hz, 1H), 2.98 (d, J=12.5 Hz, 1H), 1.95 (s, 3H). MS (m/z): MH$^+$ 407.

Hydrate 3:
$^1$H NMR (CDCl$_3$) δ 8.00 (s, 1H), 7.85 (d, J=8.5 Hz, 1H), 7.72 (d, J=8.5 Hz, 1H), 6.20 (br, s, 1H), 5.15 (br, s, 1H), 4.35 (d, J=11.5 Hz, 1H), 3.05 (d, J=11.5 Hz, 1H), 1.93 (s, 3H). MS (m/z): MH$^+$ 407.

EXAMPLE 38

4-(6-Amino-3aS-methyl-2-trifluoromethyl-3,3a-dihydro-imidazo[1,5-b]pyrazol-4-ylideneamino)-2-trifluoromethyl-benzonitrile-Hydrates

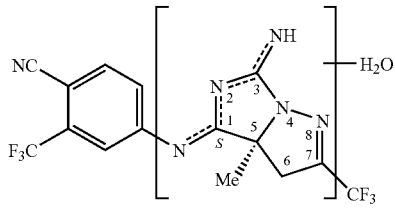

Hydrate 1 (Compound 18), Hydrate 2 (Compound 19) and Hydrate 3 (Compound 21)

Follow the procedure in Example 37, using 4-(6-amino-3aS-methyl-2-trifluoromethyl-3,3a-dihydro-imidazo[1,5-b]

pyrazol-4-ylideneamino)-2-trifluoromethyl-benzonitrile as starting material to yield the title compounds as white solids.

Hydrate 1: NMR and MS date are the same as that of Compound 16.

Hydrate 2: NMR and MS date are the same as that of Compound 17.

Hydrate 3: NMR and MS date are the same as that of Compound 20.

EXAMPLE 39

1-[4-(4-Cyano-3-trifluoromethyl-phenylimino)-3aR-methyl-2-trifluoromethyl-3a,4-dihydro-3H-imidazo[1,5-b]pyrazol-6-yl]-3-(4-iodo-phenyl)-urea-Hydrate

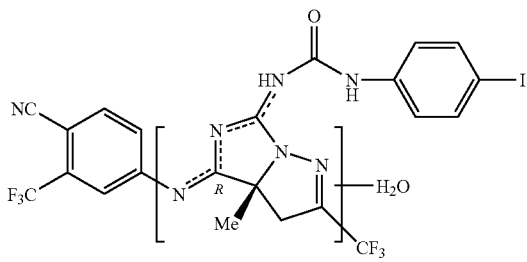

Follow the procedure in Example 36, using the hydrate 1 in Example 38 as starting material to yield the title compounds as white solids.

$^1$H NMR (CDCl$_3$) δ 9.48 (br, s, 1H), 8.05 (br, s, 1H), 7.72 (d, J=7.0 Hz, 1H), 7.62 (d, J=7.5 Hz, 2H), 7.35 (s, 1H), 7.24 (m, 3H), 6.58 (br, s, 1H), 4.37 (d, J=12.5 Hz, 1H), 3.10 (d, J=12.5 Hz, 1H), 2.02 (s, 3H). MS (m/z): MH$^+$ 652.

EXAMPLE 40

4-(6-Amino-6-ethoxy-3aR-methyl-2-trifluoromethyl-3,3a,5,6-tetrahydro-imidazo[1,5-b]pyrazol-4-ylideneamino)-2-trifluoromethyl-benzonitrile

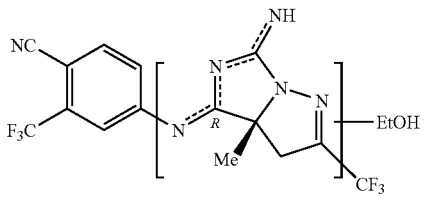

4-(6-Amino-3aR-methyl-2-trifluoromethyl-3,3a-dihydro-imidazo[1,5-b]pyrazol-4-ylideneamino)-2-trifluoromethyl-benzonitrile (1.4 mmoL) in EtOH (5 mL) was treated with NaH (60%, 3.5 mmoL) at 0° C. The reaction was then warmed to room temperature over 2 hrs. The solvent was removed and the residue was partitioned between ethyl acetate and sat. NaHCO$_3$ aq. solution. The organic layer was washed with water and brine, dried over anhydrous Na$_2$SO$_4$, filtered and concentrated to afford the crude material. The crude material was purified by flash column chromatography using hexanes: ethyl acetate 6:1 to pure ethyl acetate as eluent to afford the title compound as white solid.

$^1$H NMR (CDCl$_3$) δ 7.72 (d, J=8.0 Hz, 1H), 7.38 (s, 1H), 7.35 (br, s, 1H), 7.22 (d, J=8.0 Hz, 1H), 5.90 (br, s, 1H), 3.60 (q, J=9.5 Hz, 2H), 3.24 (abq, J=10.5 Hz, 1H), 2.85 (abq, J=10.5 Hz, 1H), 1.59 (s, 3H), 1.28 (t, J=9.5 Hz, 3H).

EXAMPLE 41

4-(6-Imino-3a-methyl-2-trifluoromethyl-3,3a-dihydro-pyrazolo[1,5-c]oxazol-4-ylideneamino)-2-trifluoromethyl-benzonitrile Compound 15

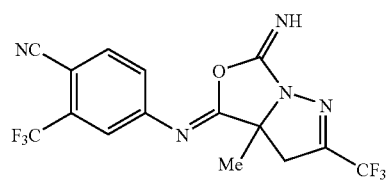

N-(4-Cyano-3-trifluoromethyl-phenyl)-3-methyl-5-trifluoromethyl-3,4-dihydro-2H-pyrazole-3-carboximidothioic acid ethyl ester (2.5 mmoL) in DMF (10 mL) was treated with KOCN (~5.0 mmoL) at room temperature. The reaction was heated to 50° C. for 2 hrs. The solid was filtered off and the residue was partitioned between ethyl acetate and water. The organic layer was washed with water and brine, dried over anhydrous Na$_2$SO$_4$, filtered and concentrated to afford the crude material. The crude material was purified by flash column chromatography using hexanes: ethyl acetate 6:1 to pure ethyl acetate as eluent to afford the title compound as white solid.

$^1$H NMR (CDCl$_3$) δ 7.80 (d, J=7.8 Hz, 1H), 7.31 (s, 1H), 7.20 (d, J=7.5 Hz, 1H), 3.60 (abq, J=11.5 Hz, 1H), 3.08 (abq, J=11.5 Hz, 1H), 1.78 (s, 3H). MS (m/z): MH$^+$ 390.

EXAMPLE 42

Ventral Prostate and Levator ani Weight in vivo Assay

Immature (approximately 50 g) castrated male Sprague Dawley rats (Charles River) were treated once daily for five days with test compound (usually given orally at 40 mg/kg in a volume of 0.3 mL, in 30% cyclodextrin or 0.5% methylcellulose vehicle), or with testosterone propionate (administered subcutaneously by injection at the nape of the neck at 5 mg/kg, in a volume of 0.1 mL in sesame oil), or with vehicle (1 mL of 30% cyclodextrin or 0.5% methylcellulose, given orally). On the sixth day, the rats were euthanized by asphyxiation in carbon dioxide. Ventral prostates and levator ani. muscle were removed and their wet weights determined.

Test compound activity was determined as the percent stimulation of tissue weight, with the vehicle-treated control group set to zero percent and the testosterone alone-treated control group set to 100%. A compound was designated as level 1 agonist active if it produced greater than or equal to 30% stimulation of levator ani or ventral prostate at 30 mg/kg. A compound was designated as level 2 agonist active if it produced greater than or equal to 5% but less than 30% stimulation of levator ani or ventral prostate at 30 mg/kg.

Representative compounds of the present invention were tested according to the procedure described, with results as listed in Table 3 below. For the compounds listed in Table 3 as "inactive", one skilled in the art will recognize that said compounds may or may not have shown an effect on prostate and/or vesical weight, rather they are listed herein as "inactive" as they did not meet the specified criteria defined above.

TABLE 3

| ID # | % Prostate Stimulation | % levator ani Stimulation |
|---|---|---|
| 1 | level 1 | level 1 |
| 2 | level 1 | level 1 |
| 3 | active level 2 | Activelevel 1 |
| 4 | inactive | inactive |
| 5 | inactive | inactive |
| 6 | inactive | inactive |
| 7 | level 2 | level 2 |
| 8 | level 2 | level 2 |
| 9 | level 2 | level 2 |
| 10 | inactive | inactive |
| 11 | level 2 | level 2 |
| 12 | NT | NT |
| 13 | level 1 | level 1 |
| 14 | level 2 | level 1 |
| 15 | level 2 | level 1 |
| 16 | level 1 | level 1 |
| 17 | level 2 | level 1 |
| 18 | inactive | level 2 |
| 19 | level 1 | level 1 |
| 20 | level 2 | level 2 |
| 21 | level 1 | level 1 |

EXAMPLE 43

Ventral Prostate and Seminal Vesicle Weight in vivo Assay

Immature (approximately 50 g) castrated male Sprague Dawley rats (Charles River) were treated once daily for five days with test compound (usually given orally at 40 mg/kg in a volume of 0.3 mL, in 30% cyclodextrin or 0.5% methylcellulose vehicle) and with testosterone propionate (given subcutaneously by injection at the nape of the neck at 2 mg/kg, in a volume of 0.1 mL in sesame oil). On the sixth day, the rats were euthanized by asphyxiation in carbon dioxide. Ventral prosatates and seminal vesicles were removed and their wet weights determined. Test compound activity was determined as the percent inhibition of testosterone-enhanced tissue weights, with a vehicle-treated control group set to zero percent and a testosterone alone-treated control group set to 100%. A compound was designated as level 1 antagonist active if it produced greater than or equal to 30% inhibition of ventral prostate or seminal vesicle at 30 mg/kg. A compound was designated as level 2 antagonist active if it produced greater than or equal to 5% but less than 30% inhibition of ventral prostate or seminal vesicle at 30 mg/kg.

Representative compounds of the present invention were tested according to the procedure described, with results as listed in Table 4 below. For the compounds listed in Table 4 as "inactive", one skilled in the art will recognize that said compounds may or may not have shown an effect on prostate and/or vesical weight, rather they are listed herein as "inactive" as they did not meet the specified criteria defined above.

TABLE 4

| ID # | Inhibition of prostate (non-weight prostate weight, mg) | Inhibition of seminal vesicle (non-weight seminal vesicle weight, mg) |
|---|---|---|
| 1 | level 2 | level 1 |
| 2 | level 2 | inactive |
| 3 | level 1 | level 2 |
| 4 | level 2 | level 2 |
| 5 | inactive | level 1 |
| 6 | inactive | level 2 |
| 7 | inactive | level 2 |
| 8 | inactive | level 2 |
| 9 | level 2 | level 1 |
| 10 | level 2 | level 2 |
| 11 | NT | NT |
| 12 | NT | NT |
| 13 | level 1 | level 2 |
| 14 | level 2 | inactive |
| 15 | level 2 | level 2 |
| 16 | level 2 | level 2 |
| 17 | inactive | leve 1 |
| 18 | inactive | inactive |
| 19 | level 1 | level 1 |
| 20 | level 2 | level 1 |
| 21 | level 1 | level 1 |

EXAMPLE 44

As a specific embodiment of an oral composition, 100 mg of the compound prepared as in Example 6 is formulated with sufficient finely divided lactose to provide a total amount of 580 to 590 mg to fill a size O hard gel capsule.

While the foregoing specification teaches the principles of the present invention, with examples provided for the purpose of illustration, it will be understood that the practice of the invention encompasses all of the usual variations, adaptations and/or modifications as come within the scope of the following claims and their equivalents.

We claim:
1. A compound of formula (I)

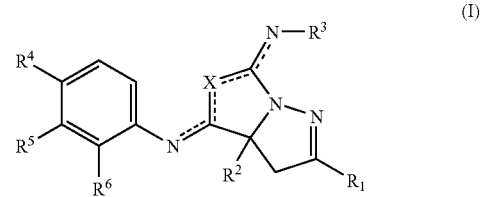

wherein
R$^1$ is selected from the group consisting of hydrogen, carboxy, alkyl, halogenated C$_{1-4}$alkyl, aryl, aralkyl, heteroaryl, —C(O)-alkyl, —C(O)-(halogenated C$_{1-4}$alkyl) and —C(O)O—C$_{1-4}$alkyl;
R$^2$ is selected from the group consisting of C$_{1-4}$alkyl and halogenated C$_{1-4}$alkyl;
X is O or NH;
R$^3$ is selected from the group consisting of C$_{1-4}$alkyl, halogenated C$_{1-4}$alkyl, —C(O)—C$_{1-4}$alkyl, —C(O)—NR$^A$—C$_{1-4}$alkyl, benzyl, —C(O)-phenyl and —C(O)—NR$^A$-phenyl; wherein R$^A$ is hydrogen or C$_{1-4}$alkyl;
R$^4$ absent or is selected from the group consisting of hydrogen, halogen, C$_{1-4}$alkyl, halogenated C$_{1-4}$alkyl, cyano, nitro, amino, C$_{1-4}$alkylamino, di(C$_{1-4}$alkyl)amino, —O—C$_{1-4}$alkyl, —S(O)$_{0-2}$—C$_{1-4}$alkyl, —NR$^B$—C(O)—C$_{1-4}$alkyl, benzyl, —O-phenyl, —C(O)-phenyl and —S(O)$_{0-2}$-phenyl; wherein R$^B$ is hydrogen or C$_{1-4}$alkyl;
R$^5$ absent or is selected from the group consisting of hydrogen, halogen, C$_{1-4}$alkyl, halogenated C$_{1-4}$alkyl, cyano, nitro, amino, C$_{1-4}$alkylamino, di(C$_{1-4}$alkyl)amino, —O—C$_{1-4}$alkyl, —S(O)$_{0-2}$—C$_{1-4}$alkyl, —NR$^B$—C (O)—C$_{1-4}$alkyl, benzyl, —O-phenyl, —C(O)-phenyl and —S(O)$_{0-2}$-phenyl; wherein R$^B$ is hydrogen or C$_{1-4}$alkyl;

R$^6$ is absent or selected from the group consisting of hydrogen, halogen, C$_{1-4}$alkyl, halogenated C$_{1-4}$alkyl, cyano, nitro, amino, —O—C$_{1-4}$alkyl and —S(O)$_{0-2}$—C$_{1-4}$alkyl;

or pharmaceutically acceptable salts and hydrates thereof.

2. A compound as in claim 1, wherein

R$^1$ is selected from the group consisting of hydrogen, carboxy, alkyl, halogenated C$_{1-4}$alkyl, aryl, aralkyl, heteroaryl, —C(O)-alkyl, —C(O)-(halogenated C$_{1-4}$alkyl) and —C(O)O—C$_{1-4}$alkyl;

R$^2$ is selected from the group consisting of C$_{1-4}$alkyl and halogenated C$_{1-4}$alkyl;

X is O or NH;

R$^3$ is selected from the group consisting of C$_{1-4}$alkyl, halogenated C$_{1-4}$alkyl, —C(O)—C$_{1-4}$alkyl, —C(O)—NR$^A$—C$_{1-4}$alkyl, benzyl, —C(O)-phenyl and —C(O)—NR$^A$-phenyl; wherein R$^A$ is hydrogen or C$_{1-4}$alkyl;

R$^4$ is absent or is selected from the group consisting of hydrogen, halogen, C$_{1-4}$alkyl, halogenated C$_{1-4}$alkyl, cyano, nitro, amino, C$_{1-4}$alkylamino, di(C$_{1-4}$alkyl)amino, —O—C$_{1-4}$alkyl, —S(O)$_{0-2}$—C$_{1-4}$alkyl, —NR$^B$—C(O)—C$_{1-4}$alkyl, benzyl, —O-phenyl, —C(O)-phenyl and —S(O)$_{0-2}$-phenyl; wherein R$^B$ is hydrogen or C$_{1-4}$alkyl;

R$^5$ is absent or is selected from the group consisting of hydrogen, halogen, C$_{1-4}$alkyl, halogenated C$_{1-4}$alkyl, cyano, nitro, amino, C$_{1-4}$alkylamino, di(C$_{1-4}$alkyl)amino, —O—C$_{1-4}$alkyl, —S(O)$_{0-2}$—C$_{1-4}$alkyl, —NR$^B$—C(O)—C$_{1-4}$alkyl, benzyl, —O-phenyl, —C(O)-phenyl and —S(O)$_{0-2}$-phenyl; wherein R$^B$ is hydrogen or C$_{1-4}$alkyl;

R$^6$ is absent or selected from the group consisting of hydrogen, halogen, C$_{1-4}$alkyl, halogenated C$_{1-4}$alkyl, cyano, nitro, amino, —O—C$_{1-4}$alkyl and —S(O)$_{0-2}$—C$_{1-4}$alkyl.

3. A compound as in claim 2, wherein

R$^1$ is selected from the group consisting of hydrogen, carboxy, alkyl, halogenated C$_{1-4}$alkyl, aryl, aralkyl, heteroaryl, —C(O)-alkyl, —C(O)-(halogenated C$_{1-4}$alkyl) and —C(O)O—C$_{1-4}$alkyl;

R$^2$ is selected from the group consisting of C$_{1-4}$alkyl and halogenated C$_{1-4}$alkyl;

X is O or NH;

R$^3$ is selected from the group consisting of C$_{1-4}$alkyl, halogenated C$_{1-4}$alkyl, —C(O)—C$_{1-4}$alkyl, —C(O)—NR$^A$—C$_{1-4}$alkyl, benzyl, —C(O)-phenyl and —C(O)—NR$^A$-phenyl; wherein R$^A$ is hydrogen or C$_{1-4}$alkyl;

R$^4$ is absent or is selected from the group consisting of hydrogen, halogen, C$_{1-4}$alkyl, halogenated C$_{1-4}$alkyl, cyano, nitro, amino, C$_{1-4}$alkylamino, di(C$_{1-4}$alkyl)amino, —O—C$_{1-4}$alkyl, —S(O)$_{0-2}$—C$_{1-4}$alkyl, —NR$^B$—C(O)—C$_{1-4}$alkyl, benzyl, —O-phenyl, —C(O)-phenyl and —S(O)$_{0-2}$-phenyl; wherein R$^B$ is hydrogen or C$_{1-4}$alkyl;

R$^5$ is absent or is selected from the group consisting of hydrogen, halogen, C$_{1-4}$alkyl, halogenated C$_{1-4}$alkyl, cyano, nitro, amino, C$_{1-4}$alkylamino, di(C$_{1-4}$alkyl)amino, —O—C$_{1-4}$alkyl, —S(O)$_{0-2}$—C$_{1-4}$alkyl, —NR$^B$—C(O)—C$_{1-4}$alkyl, benzyl, —O-phenyl, —C(O)-phenyl and —S(O)$_{0-2}$-phenyl; wherein R$^B$ is hydrogen or C$_{1-4}$alkyl;

R$^6$ is absent or selected from the group consisting of hydrogen, halogen, C$_{1-4}$alkyl, halogenated C$_{1-4}$alkyl, cyano, nitro, amino, —O—C$_{1-4}$alkyl and —S(O)$_{0-2}$—C$_{1-4}$alkyl.

4. A compound as in claim 3, wherein

R$^1$ is selected from the group consisting of hydrogen, trifluoromethyl, 2,3,4,5,6-pentafluorophenyl and ethoxy carbonyl;

R$^2$ is methyl;

R$^3$ is hydrogen or trifluoromethyl carbonyl;

X is O or N;

R$^4$ is selected from the group consisting of chloro, cyano and nitro;

R$^5$ is trifluoromethyl;

R$^6$ is H or ethyl.

5. A compound as in claim 4, selected from the group consisting of 4-(6-Amino-3R-methyl-2-trifluoromethyl-3,3a-dihydro-imidazo[1,5-b]pyrazol-4-ylideneamino)-2-trifluoromethyl-benzonitrile;

4-(6-Amino-3a R-methyl-2-trifluoromethyl-3,3a-dihydro-imidazo[1,5-b]pyrazol-4-ylideneamino)-2-trifluoromethyl-benzonitrile;

4-(6-Amino-3aS-methyl-2-trifluoromethyl-3,3a-dihydro-imidazo[1,5-b]pyrazol-4-ylideneamino)-2-trifluoromethyl-benzonitrile;

N-[4-(4-Cyano-3-trifluoromethyl-phenylimino)-3aR-methyl-2-trifluoromethyl-3a,4-dihydro-3H-imidazo[1,5-b]pyrazol-6-yl]-2,2,2-trifluoro-acetamide;

Hydrates of 4-(6-Amino-3aR-methyl-2-trifluoromethyl-3,3a-dihydro-imidazo[1,5-b]pyrazol-4-ylideneamino)-2-trifluoromethyl-benzonitrile; and Hydrates of 4-(6-Amino-3aS-methyl-2-trifluoromethyl-3,3a-dihydro-imidazo[1,5-b]pyrazol-4-ylideneamino)-2-trifluoromethyl-benzonitrile.

6. A pharmaceutical composition comprising a pharmaceutically acceptable carrier and a compound of claim 1.

7. A method of treating a disorder mediated by an androgen receptor, in a subject in need thereof comprising administering to the subject a therapeutically effective amount of the compound of claim 1, wherein the disorder mediated by an androgen receptor is selected from the group consisting of prostate carcinoma, benign prostatic hyperplasia (BPH), hirsitutism, alopecia, anorexia nervosa, breast cancer, acne, male contraception, male performance, and cachexia.

8. A method as in claim 7, wherein the disorder mediated by an androgen receptor is male contraception or male performance.

9. A method of treating a condition selected from the group consisting of prostate carcinoma, benign prostatic hyperplasia (BPH), hirsitutism, alopecia, anorexia nervosa, breast cancer, acne, cachexia, male contraception, and male performance, in a subject in need thereof comprising administering to the subject a therapeutically effective amount of the compound of claim 1.

* * * * *